(12) United States Patent
Weissleder et al.

(10) Patent No.: US 9,869,619 B2
(45) Date of Patent: *Jan. 16, 2018

(54) SELF-ASSEMBLED MAGNETIC ARRAYS

(71) Applicant: The General Hospital Corporation, Boston, MA (US)

(72) Inventors: Ralph Weissleder, Peabody, MA (US); Hakho Lee, Acton, MA (US); David Issadore, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/393,402

(22) Filed: Dec. 29, 2016

(65) Prior Publication Data
US 2017/0212021 A1     Jul. 27, 2017

Related U.S. Application Data

(63) Continuation of application No. 13/825,762, filed as application No. PCT/US2011/053466 on Sep. 27, 2011, now Pat. No. 9,532,729.

(60) Provisional application No. 61/386,759, filed on Sep. 27, 2010.

(51) Int. Cl.
| | | |
|---|---|---|
| *G01N 1/40* | (2006.01) | |
| *B03C 1/033* | (2006.01) | |
| *H01F 1/047* | (2006.01) | |
| *G01N 33/483* | (2006.01) | |
| *A61B 5/055* | (2006.01) | |
| *H01F 10/00* | (2006.01) | |

(52) U.S. Cl.
CPC ........... *G01N 1/4077* (2013.01); *A61B 5/055* (2013.01); *B03C 1/0332* (2013.01); *G01N 33/4833* (2013.01); *H01F 1/047* (2013.01); *H01F 10/007* (2013.01); *B03C 2201/18* (2013.01); *G01N 2001/4088* (2013.01); *G01N 2610/00* (2013.01)

(58) Field of Classification Search
CPC ....... A61B 5/055; B03C 1/0332; B03C 1/288; B03C 2201/26; B03C 2201/18; H01F 1/009; H01F 1/068; H01F 1/047; H01F 10/007; G01R 33/383; G01N 1/4077; G01N 33/4833; G01N 2001/4088; G01N 2610/00

See application file for complete search history.

(56) References Cited

U.S. PATENT DOCUMENTS

| | | |
|---|---|---|
| 5,981,053 A | 11/1999 | Naylor |
| 6,749,750 B2 | 6/2004 | Barbera-Guillem |
| 6,858,184 B2 | 2/2005 | Pelrine et al. |

(Continued)

FOREIGN PATENT DOCUMENTS

| | | |
|---|---|---|
| EP | 1580555 | 9/2005 |

OTHER PUBLICATIONS

Adams et al., "Multitarget magnetic activated cell sorter," PNAS 2008, 105(47):18165-18170, 6 pages.

(Continued)

*Primary Examiner* — David C Mellon
(74) *Attorney, Agent, or Firm* — Fish & Richardson P.C.

(57) ABSTRACT

A magnetic device includes a substrate and an array including a plurality of magnetic particles, in which a magnetic dipole moment direction of each magnetic particle in a majority of the magnetic particles in the array alternates with respect to a magnetic dipole direction of a directly adjacent magnetic particle or directly adjacent magnetic particles in the array.

10 Claims, 18 Drawing Sheets

(56) References Cited

U.S. PATENT DOCUMENTS

| | | | |
|---|---|---|---|
| 7,041,394 | B2 | 5/2006 | Weller |
| 7,931,577 | B2 | 4/2011 | Bove |
| 8,951,782 | B2 | 2/2015 | Chang |
| 2002/0001855 | A1 | 1/2002 | Prentiss et al. |
| 2003/0040129 | A1 | 2/2003 | Shah |
| 2004/0009614 | A1 | 1/2004 | Ahn et al. |
| 2004/0018611 | A1 | 1/2004 | Ward |
| 2009/0053799 | A1 | 2/2009 | Chang-Yen |
| 2010/0154556 | A1 | 6/2010 | Huiming |
| 2012/0052286 | A1 | 3/2012 | Norwood |

OTHER PUBLICATIONS

Chalmers et al., "Analytical magnetic techniques in biology," Laboratory Techniques in Biochemistry and Molecular Biology 2008, 32(8):225-247, 24 pages.

Antoine et al., "Lymphoid Cell Fractionation on Magnetic Polyacrylamide-Agarose Beads," Immunochemistry 1978, 15:443-452, 10 pages.

Chalmers et al., "Flow Through, Immunomagnetic Cell Separation," Biotechnol. Prog. 1998, 14:141-148, 8 pages.

Chalmers et al., "Preparative applications of magnetic separation in biology and medicine," Laboratory Techniques in Biochemistry and Molecular Biology 2008, 32(9):249-264, 16 pages.

Cristofanilli et al., "Circulating Tumor Cells, Disease Progression, and Survival in Metastatic Breast Cancer," N Engl J Med 2004, 351:781-791, 11 pages.

Croat et al., "Pr—Fe and Nd—Fe-based materials: A new class of high-performance permanent magnets (invited)," J. Appl. Phys. 1984, 5(6):2078-2082, 5 pages.

Csordas et al., "Detection of Proteins in Serum by Micromagnetic Aptamer PCR (MAP) Technology," Angew. Chem. Int. Ed. 2010, 49:355-358, 4 pages.

Deng et al., "Manipulation of magnetic microbeads in suspension using micromagnetic systems fabricated with soft lithography," Appl. Phys. Lett. 2001, 78(12):1775-1777, 3 pages.

Drndic et al., "Properties of microelectromagnet mirrors as reflectors of cold Rb atoms," Physical Review A 1999, 60(5):4012-4015, 4 pages.

Feynman et al., "The Feynman Lectures on Physics, vol. II, Mainly Electromagnetism and Matter," Addison-Wesley Publishing Company 1964 Chp. 1:1-7-1-10, 9 pages.

Franzreb et al., "Protein purification using magnetic adsorbent particles," Appl. Mcrobiol Biotechnol 2006, 70:505-516, 12 pages.

Gijs, "Magnetic bead handling on-chip: new opportunities for analytical applications," Microfluid Nanofluid 2004, 1:22-40, 19 pages.

Gottlieb et al., "Pneumocystis Carinii Pneumonia and Mucosal Candidiasis in Previously Healthy Homosexual Men, Evidence of a New Acquired Cellular Immunodeficiency," N Engl J Med 1981, 305(24):1425-1431, 7 pages.

Han et al., "Continuous magnetophoretic separation of blood cells in microdevice format," J. Appl. Phys. 2004, 96(10):5797-5802, 6 pages.

Inglis et al., "Microfluidic high gradient magnetic cell separation," J. Appl. Phys. 2006, 99:08K101-1-08K101-3, 3 pages.

Kim et al., "Simultaneous sorting of multiple bacterial targets using integrated Dielectrophoretic-Magnetic Activated Cell Sorter," Lab Chip 2009, 9:2313-2318, 6 pages.

Lagasse et al., "Purified hematopoietic stem cells can differentiate into hepatocytes in vivo," Nature Medicine 6(11):1229-1234, 6 pages.

Lee et al., "Manipulation of biological cells using a microelectromagnet matrix," Appl. Phys. Lett. 2004, 85(6) 1063-1065, 3 pages.

Lou et al., "Micromagnetic selection of aptamers in microfluidic channels," PNAS 2009, 106(9):2989-2994, 6 pages.

Mattanovich et al., "Applications of cell sorting in biotechnology," Microbial Cell Factories 2006, 5(12), 11 pages.

Melville et al., "Direct magnetic separation of red cells from whole blood," Nature 1975, 255:706, 1 page.

Meye et al., "Isolation and enrichment of urologic tumor cells in blood samples by a semi-automated CD45 depletion autoMACS protocol," International Journal of Oncology 2002, 21:521-530, 10 pages.

Miltenyi et al., "High Gradient Magnetic Cell Separation with MACS1," Cytometry 1990, 11:231-238, 8 pages.

Mykhaylyk et al., "Generation of magnetic nonviral gene transfer agents and magnetofection in vitro," Nature Protocols 2007, 2(10):2391-2411, 21 pages.

Nagrath et al., "Isolation of rare circulating tumour cells in cancer patients by microchip technology," Nature 2007, 450:1235-1239, 7 pages.

Oberteuffer et al., "High Gradient Magnetic Filtration of Steel Mill Process and Waste Waters," IEEE Transactions on Magnetics 1975, 11(5):1591-1593, 3 pages.

Orkin, "Stem cell alchemy," Nature Medicine 2000, 6(11):1212-1213, 2 pages.

Pamme et al., "Continuous sorting of magnetic cells via on-chip free-flow magnetophoresis," Lab Chip 2006, 6:974-980, 7 pages.

Rozenfel'd, "Calculation of the Field of a Lattice of Point Magnetic Dipoles," Physics of the Solid State 2000, 42(9):1681-1687, 8 pages.

Vieira et al., "Magnetic Wire Traps and Programmable Manipulation of Biological Cells," The Am. Phys. Soc. 2009, 103(12):128101-1-4, 4 pages.

Xia et al., "Combined microfluidic-micromagnetic separation of living cells in continuous flow," Biomed Microdevices 2006, 8:299-308, 10 pages.

International Search Report and Written Opinion dated Apr. 23, 2012 issued in international application No. PCT/US2011/053466, 9 pgs.

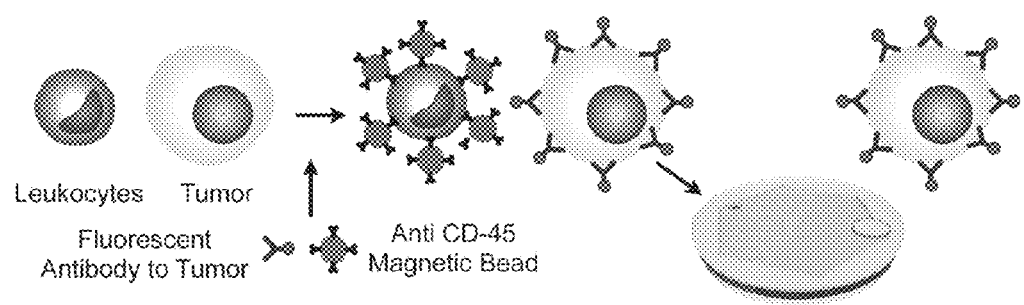
FIG. 13
FIG. 14A
1/10 (Tumor/Leukocyte)
FIG. 14C
1/100
FIG. 14E
1/1000
Input
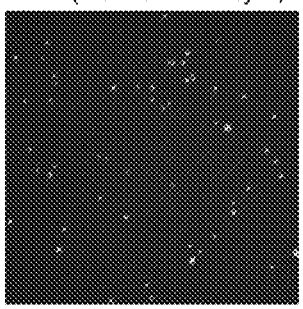 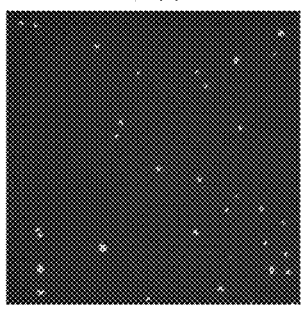 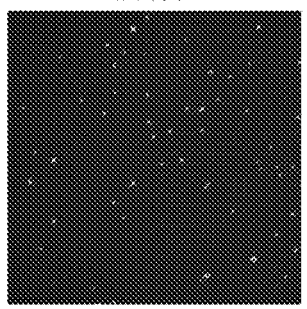
Filter
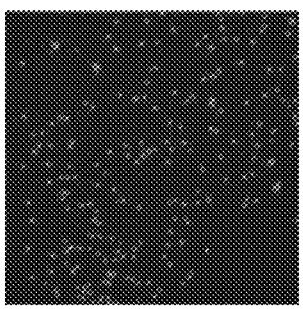
FIG. 14B
FIG. 14D
FIG. 14F

SELF-ASSEMBLED MAGNETIC ARRAYS

PRIORITY CLAIM

This application is a continuation of U.S. patent application Ser. No. 13/825,762, having a 371(e) filing date of Jun. 18, 2013, which is a 35 U.S.C. § 371 national stage application of International Application No. PCT/US2011/053466, filed Sep. 27, 2011, which claims the benefit of U.S. Provisional Patent Application No. 61/386,759, filed Sep. 27, 2010. The entire contents of the foregoing applications are incorporated herein by reference.

FIELD OF THE INVENTION

The present disclosure relates to self-assembled magnetic arrays.

BACKGROUND

Devices that produce magnetic fields can have broad applications in biotechnology and medicine. For example, magnetic fields generated by such devices have applications in cancer diagnostics, drug discovery, and stem cell research, among others. One particular area includes magnetic separation of cells, in which cells of interest are attached to magnetic biomarkers in a solution and the solution is then introduced into an area having a magnetic field. The magnetic field serves to isolate and/or filter the cells having the attached biomarkers for subsequent analysis, modification, or use.

SUMMARY

The present disclosure relates to self-assembled magnetic (SAM) devices and methods for their fabrication and use. Each magnetic device includes an array of self-assembled magnetized particles, in which the magnetic dipole direction of each particle in a majority of the magnetized particles is substantially opposite to the magnetic dipole direction of a directly adjacent particle or directly adjacent particles in the array. The magnetic field contribution from each magnetized particle can provide the array with an overall magnetic field having a high magnitude and field gradient, thus producing a strong magnetic force. The strong magnetic forces of the self-assembled device can be used to enhance applications such as, for example, magnetotransfection and sorting/filtering of cells and/or molecules and other analytes. In some cases, the self-assembled magnetic device also can be used to generate polarizing fields for various magnetic devices including, for example, nuclear magnetic resonance devices, Hall sensors, and magnetoresistive devices.

In one aspect, the subject matter described herein can be embodied in magnetic devices that include a substrate and an array including a plurality of magnetic particles on the substrate. A magnetic dipole moment direction of each magnetic particle in a majority of the magnetic particles in the array alternates with respect to a magnetic dipole direction of a directly adjacent magnetic particle in the array.

In some implementations, the magnetic particles in the array include permanent magnets. In some cases, the magnetic particles in the array include superparamagnetic material. In certain implementations, each magnetic particle in the array is composed of NdFeB, SmCo, FePt, or iron oxide.

In some implementations, the magnetic devices further include a suspension layer, in which the array of magnetic particles is located, e.g., dispersed, within the suspension layer. The suspension layer can include a curable polymer. The polymer can include any one or a combination of polyurethane, epoxy, poly(methyl methacrylate) (PMMA), or polydimethylsiloxane (PDMS).

In some cases, the magnetic devices further include one or more fluid flow channels, e.g., multiple fluid flow channels, adjacent to the array. In certain implementations, the magnetic devices further include a cell culture medium container adjacent to the array. One or more of the fluid flow channels can include a chaotic mixer.

In some implementations, the magnetic devices further include a first layer and a second layer, in which the array including the plurality of magnetic particles is in contact with a surface of the first layer and is between the first and second layers.

In some cases, each magnetic particle in the array has a size greater than or equal to about 100 nm and less than about 1 mm. In certain cases, the plurality of magnetic particles in the array is close-packed.

In another aspect, the subject matter disclosed herein can be embodied as methods of fabricating magnetic devices. These methods include providing a mixture containing a plurality of magnetizable particles, applying a magnetic field to the mixture to magnetize the plurality of magnetizable particles, and forming an array including the plurality of magnetized particles, in which a magnetic dipole moment direction of a magnetized particle in the array alternates with respect to a magnetic dipole moment direction of a directly adjacent magnetized particle or directly adjacent magnetized particles in the array. In some implementations, the mixture containing the plurality of magnetized particles includes a solvent and the plurality of magnetized particles is contained within the solvent. Forming the array can include depositing the mixture containing the plurality of magnetized particles on a first layer or substrate and evaporating the solvent to leave the array including the plurality of magnetized particles on the first layer.

In certain cases, forming the array includes allowing the magnetized particles to self-assemble into the array of magnetized particles.

In some cases, the mixture containing the plurality of magnetized particles includes a curable polymer and the plurality of magnetized particles is within the curable polymer, and forming the array includes curing the mixture containing the plurality of magnetized particles.

In certain implementations, curing the mixture includes heating the mixture containing the plurality of magnetized particles or applying ultraviolet radiation to the mixture containing the plurality of magnetized particles. Forming the array can further include allowing the magnetized particles to self-assemble into the array of magnetized particles prior to or during curing. Once the mixture is cured, the orientation of the particles is fixed.

In some implementations, the methods further include forming a fluid flow channel adjacent to the array of magnetized particles. In some cases, the methods further include forming a cell culture chamber adjacent to array of magnetized particles.

In some implementations, the methods further include forming multiple fluid flow channels adjacent to the array of magnetized particles. Forming the fluid flow channels can include forming a chaotic mixer in one or more of the channels.

In another aspect, the subject matter disclosed herein can embody methods of sorting target particles. These methods include flowing a suspension containing a first particle and a second different particle through a fluid flow channel of one or more magnetic devices, e.g., arranged in series or parallel, to sort the first particle from the second particle based on a difference in magnetic susceptibility between the first particle and the second particle. The magnetic devices can include a substrate and an array including a plurality of magnetic particles on the substrate. A magnetic dipole moment direction of a magnetic particle in the array alternates with respect to a magnetic dipole direction of a directly adjacent magnetic particle or directly adjacent magnetic particles in the array.

In another aspect, the subject matter disclosed herein can embody methods of sorting target particles, in which the method includes flowing a suspension containing first particles and second different particles through multiple fluid flow channels of a magnetic device to sort the first particles from the second particles based on a difference in magnetic susceptibility between the first particles and the second particles. One or more multi-channel devices can be arranged in series or parallel, e.g., with one or more simple-channel devices as described herein.

In another aspect, the subject matter disclosed herein include methods of magnetotransfection that include forming a cell culture chamber on a magnetic device as described herein, in which the cell culture chamber includes a plurality of cells submerged in a cell culture solution in the chamber, and adding a plurality of magnetic particles to the cell culture solution, in which each of the magnetic particles is coupled to genetic material, such that a magnetic force from the magnetic device pulls the magnetic nanoparticles toward the cells and forces one or more of the magnetic particles into at least one of the cells. The magnetic device includes a substrate and an array including a plurality of magnetic particles on the substrate. A magnetic dipole moment direction of each magnetic particle in the array alternates with respect to a magnetic dipole direction of each directly adjacent magnetic particle in the array.

As used herein, close-packed particles are particles densely arranged in a lattice/array such that directly adjacent particles in the array are touching or nearly touching (e.g., the particles are close enough that the magnetic force of one particle is affected by the magnetic force of the adjacent particle). Nearly touching particles include, but are not limited to, directly adjacent particles that are separated by about 0.5 nm or less, about 1 nm or less, about 5 nm or less, about 50 nm or less, about 100 nm or less, about 1 µm or less, about 10 µm or less, or about 100 µm or less, depending on the size and mature of the particles. The "pitch" between two directly adjacent and close-packed particles is the distance between the center of one of the particles and the center of the other particle.

"Superparamagnetic particles" are particles that are composed of a single magnetic domain in thermodynamic equilibrium. Such particles exhibit a negligible magnetic moment when not exposed to an external magnetic field, but assume a large magnetic moment and magnetic susceptibility when an external field is applied. These particles can be in the nanoparticle or microparticle size range.

Embodiments of the invention provide several advantages. For example, in some implementations, the self-assembled magnetic arrays can be used to generate magnetic field gradients exhibiting high magnetic forces. In some cases, the self-assembled magnetic devices can be used in a filtering device to separate or filter, from a solution, analytes, e.g., cells, having particular magnetic properties from analytes having different or no magnetic properties. Alternatively, or in addition, the self-assembled magnetic devices can be used in a filtering device to separate or filter analytes that are coupled to magnetic markers from analytes that are not coupled to magnetic markers. The large forces exhibited by the magnetic field of the self-assembled array can, in certain instances, lead to enhanced sorting efficiency for the filtering devices. Due to the self-assembly of magnetic particles in the array, fabrication time and costs of devices that include the arrays can be reduced relative to devices that rely on alternative sources for generating magnetic field gradients.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, the figures and from the claims.

BRIEF DESCRIPTION OF DRAWINGS

FIG. 13 is a schematic that illustrates an exemplary conjugation and tagging process.

FIGS. 14A-14F are fluorescence micrographs of the input and the output of a self-assembled magnetic array filter for suspensions having different concentrations of tumor cells to leukocytes.

DETAILED DESCRIPTION

The present disclosure relates to self-assembled magnetic (SAM) devices and methods for their fabrication and use. Each magnetic device includes an array of self-assembled magnetized particles, in which the magnetic dipole direction of each particle is substantially opposite to the magnetic dipole direction of each directly adjacent particle(s) in the array. The magnetic field contribution from each magnetized particle can provide the array with an overall magnetic field having a high magnitude and field gradient, thus producing a strong magnetic force. The strong magnetic forces of the self-assembled device can be used to enhance applications such as, for example, magnetotransfection and sorting/filtering of cells and/or small molecules. In some cases, the self-assembled magnetic device also can be used to generate polarizing fields for various magnetic devices including, for example, nuclear magnetic resonance devices, Hall sensors, and magnetoresistive devices.

Self-Assembled Magnetic Devices

Figure 1:
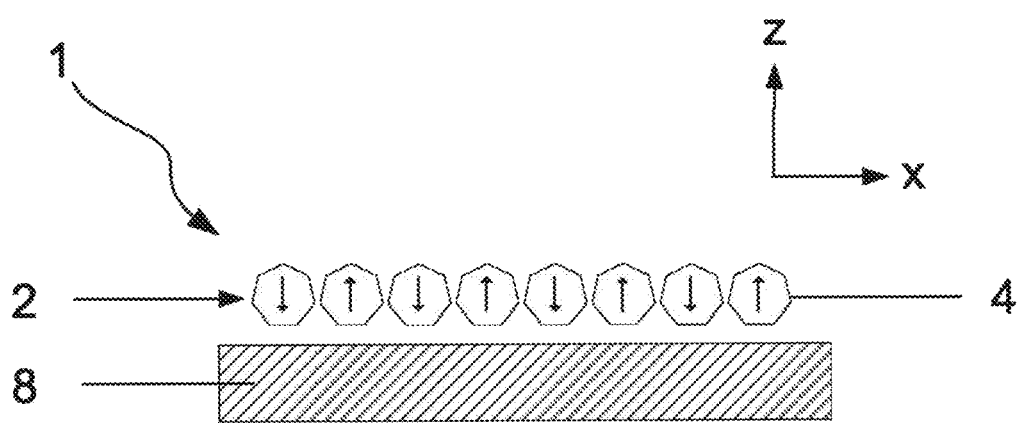
FIG. 1 is a schematic diagram that shows a cross-section of an exemplary magnetic array for producing localized magnetic field gradients.

FIG. 1 shows a cross-section of an exemplary device 1 for producing localized magnetic field gradients. The device 1 includes a substrate 8 on which an array 2 of self-assembled magnetized particles 4 are positioned and extend along the x-axis. In general, although not necessary, the magnetized particles 4 are close-packed, i.e., the particles 4 are densely arranged in a lattice/array such that directly adjacent particles 4 are touching or nearly touching (e.g., directly adjacent particles are separated by about 0.5 nm or less, about 1 nm or less, about 5 nm or less, about 50 nm or less, about 100 nm or less, about 1 µm or less, about 10 µm or less, or about 100 µm or less), depending on the size and nature of the particles. A direction of each particle's magnetic dipole moment 6 (depicted by arrows in FIG. 1) alternates with respect to the direction of a directly adjacent particle's magnetic dipole moment 6. For example, as shown in FIG. 1, the magnetic dipole moment 6 of each magnetized particle 4 in the array 2 is in a substantially opposite direction to a magnetic dipole moment 6 of each directly adjacent magnetized particle 4. It is not necessary that every particle 4 in the array 2 has a magnetic dipole moment that is opposite in direction to the magnetic dipole moment of each directly adjacent particle in the array 2. For example, in some implementations, a majority of particles in the array 2 has a magnetic dipole moment that is opposite in direction to a magnetic dipole moment of the directly adjacent particles in the array 2, whereas at least some particles 4 in the array 2 have a magnetic dipole moment that is in the same direction as a magnetic dipole moment of a directly adjacent particle. The antiparallel configuration of the dipole moments in the array 2 creates magnetic field patterns that decay exponentially in space, giving rise to large magnetic field gradients ∇B, where B is the magnetic field vector. In the example shown in FIG. 1, the magnetic field patterns decay in the z-direction, away from the array 2. The array 2 of magnetized particles 4 is formed through self-assembly. In particular, a group of magnetized particles 4 will, depending on surrounding conditions, tend to form an antiparallel configuration of dipole moments to minimize the magnetic energy across the array 2.

The strength of the magnetic force above the array 2 is due to both the magnitude of the magnetic field, |B|, and the field gradients, ∇B, resulting from the alternating dipole moment configuration. By employing magnetized particles 4 formed from highly magnetic material (and thus high |B|), it is possible to generate strong magnetic forces in regions above the array 2. Such strong magnetic forces can be used to manipulate, within those regions, target analytes having magnetically susceptible properties.

In some implementations, the particles 4 can be formed from materials that have been permanently magnetized. Examples of permanent magnetic materials that can be used as the particles 4 include, but are not limited to, NdFeB, SmCo, ferrite, iron, nickel, and cobalt. NdFeB is an inexpensive and readily available magnetizable material that has high remanence (magnetic field strength) and a high energy product (magnetic energy density). SmCo has a slightly lower magnetic energy product than NdFeB, but has greater temperature stability. Accordingly, SmCo can be useful in applications where it is preferable to have temperature-stable magnetic fields, such as nuclear magnetic resonance spectroscopy. Ferrite can include magnetized iron oxides such as FeO, $Fe_2O_3$, and $Fe_3O_4$, among others.

In some implementations, the particles 4 can be formed from superparamagnetic materials. Superparamagnetic particles are particles that are composed of a single magnetic domain in thermodynamic equilibrium and which exhibit a large magnetic moment and magnetic susceptibility upon exposure to an external magnetic field. Generally, the size of a superparamagnetic particle is about 100 nm or less. Superparamagnetism is a feature of ferromagnetic particles coming from their small size. Examples include iron oxides of the $Fe_3O_4$ magnetite type and $\gamma Fe_2O_3$ type (maghemite). The particles can be formed from other superparamagnetic materials as well. Although an array 2 that employs magnetized particles 4 formed from superparamagnetic material would require an external magnetic field to turn the magnetic particles 4 "on" (i.e., to magnetize the particles 4), it would also enable the option of turning the magnetic field "off" (i.e., demagnetizing the particles 4) by removing the external magnetic field. In contrast, the magnetic field of an array 2 containing particles 4 formed from permanent magnets would always be "on." Other magnetic materials from which the particles 4 can be formed include, but are not limited to, FePt, doped-Alnico, $MnFe_2O_4$, $CoFe_2O_4$, $NiFe_2O_4$, and $ZnMnFe_2O_4$.

In the example of FIG. 1, each magnetized particle 4 has a generally circular cross-section (spherical in 3 dimensions) with irregular surface variations, although other shapes, such as cylindrical, spheroidal, and whisker-like, are possible as well. The magnetized particles 4 also can have various sizes.

For example, in some cases, the magnetized particles can have an average maximum dimension that ranges anywhere from about 50 nm to about several millimeters, including, for example, about 100 nm, about 500 nm, about 1 µm, about 100 µm, or about 1 mm. If the magnetized particles 4 are close-packed, the pitch between the particles 4 (i.e., the distance between the centers of each particle) can be controlled by selecting the particle size. As shown in the example of FIG. 1, the magnetic particles 4 of the array 2 can be formed in a single monolayer that has a thickness on the order of the particle size. However, arrays having thicknesses greater than the particle size also can be formed, in which the array includes multiple layers of magnetized particles 4. It should be noted that although the array 2 in the example of FIG. 1 is shown to extend along one direction (x-direction), such arrays also can be arranged in two or three dimensions. For example, the array 2 of magnetized particles 4 shown in FIG. 1 also can extend into the page (y-direction).

The length-scale of the magnetic field gradient can be controlled based on the size of the magnetized particles in the array. The strength of the magnetic force (proportional to $(B \cdot \nabla)B$) above a two-dimensional (2D) array of alternating dipoles (using the coordinates shown in FIG. 1, where the x-direction and y-direction are in the plane of the array and the z-direction extends away from the array) can be expressed in an analytical form, $$|(\vec{B} \cdot \vec{\nabla})\vec{B}| = \sum_{k,l} F_{k,l} e^{-2\pi|z|\sqrt{(k/a)^2+(l/b)^2}} \quad \text{(Eq. 1)}$$

where a and b are the pitch (e.g., the particle center-to-particle center distance) between directly adjacent magnetized particles 4 (and thus between magnetic dipoles) in the x- and y-directions, respectively, z is the distance along the z-direction, $F_{k,l}$ are the Fourier components of magnetic field, and k and l are the indices for the Fourier components of the field. In an array of magnetized particles 4, both a and b are established by the separation of the magnetic grains as well as the size of the magnetic grains. For a given grain size, the minimum values of a and b are obtained when the particles 4 are close-packed. The Fourier components vanish and the magnetic field B goes to zero far from the array in the z-direction. Using the foregoing relationship, the strength of the magnetic field gradient and the distance that the gradient extends from the magnet can be traded-off and engineered for specific applications.

The field from an individual magnetic dipole of a magnetized particle 4 is given by the expression:

$$B(r, c) = \frac{\mu_o}{4\pi} \frac{3r\{m \cdot (r-c)\} - m(r-c)^2}{|r-c|^5}, \quad \text{(Eq. 2)}$$

where c is the vector location of the magnetic moment, r is the vector location at which the field is measured, and m is the magnetic moment. For a periodic array of magnetic dipoles, arranged in a 2D square lattice with a spacing a between magnetic dipoles, the total magnetic field can be expressed as the superposition of the field from each magnetic moment:

$$B(r) = \sum_{i,j} B(r, c_{ij}). \quad \text{(Eq. 3)}$$

Figures 2A, 2B:
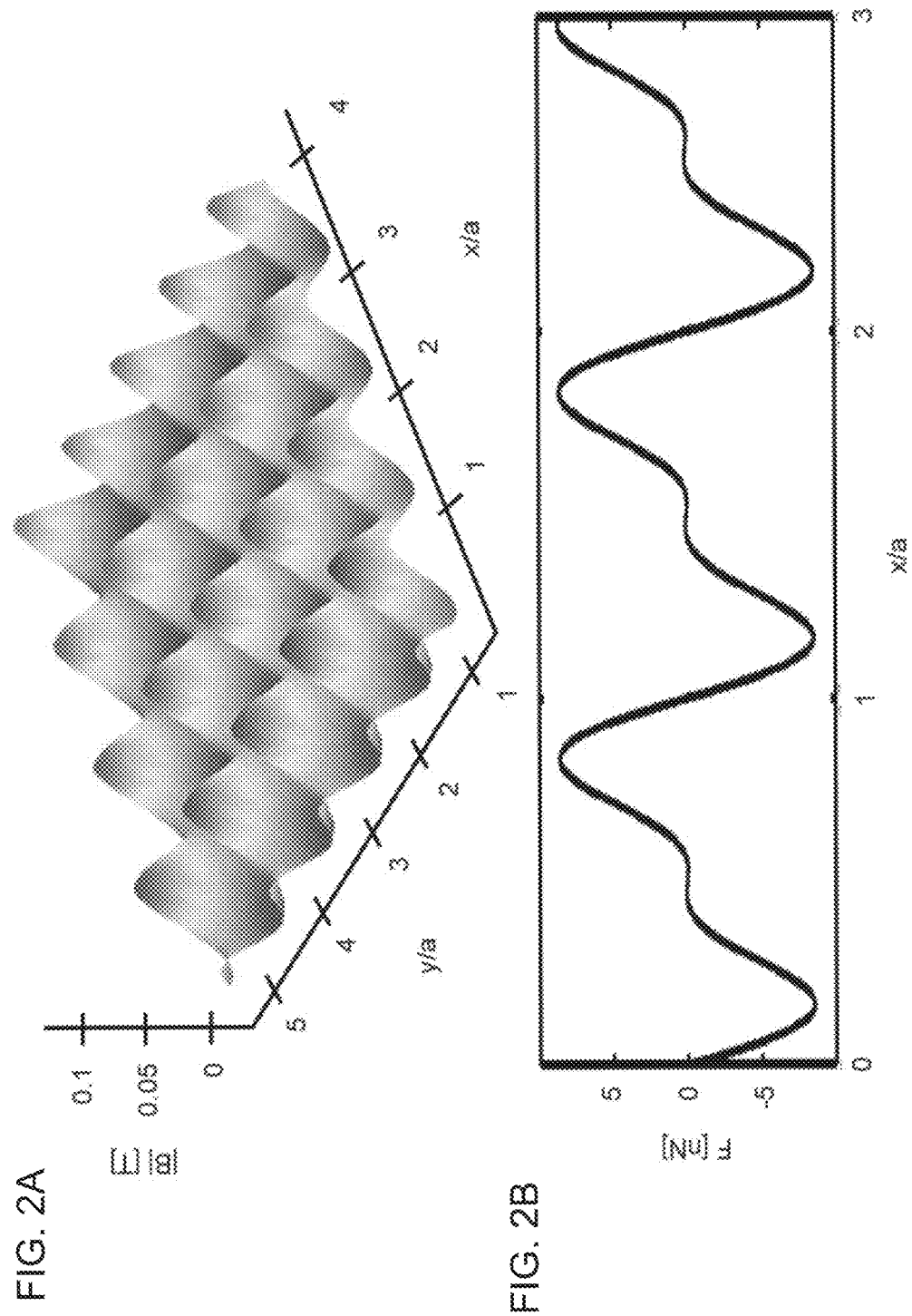
FIG. 2A is a graph of simulated magnetic field strength.
FIG. 2B is a graph showing simulated magnetic force.

FIG. 2a is a graph of simulated magnetic field strength created by a 2D square lattice of magnetic dipoles at a distance d=a away from the lattice in the z-direction, where the lattice extends over the x and y directions. The field strength forms an egg carton pattern, creating many magnetic traps that have a size and periodicity set by the spacing a between magnetic dipoles and the distance d from the lattice.

To form an analytical expression for the field at distances close to the array, the field can be expressed as a sum of periodic functions in a Fourier series, giving the solution:

$$B(r) = \frac{8\pi^2 \mu_o}{a^2} e^{-2\pi Q|z|}[A\cos(2\pi kx/a)\cos(2\pi ly/a) + \quad \text{(Eq. 4)}$$
$$B\cos(2\pi kx/a)\sin(2\pi ly/a) + C\sin(2\pi kx/a)\cos(2\pi ly/a) +$$
$$D\sin(2\pi kx/a)\sin(2\pi ly/a)]$$

where the term k=l=0 is excluded, and the terms A, B, C, D are constants set by the boundary conditions, and $$Q_{l,k} = \sqrt{\left(\frac{k}{a}\right)^2 + \left(\frac{l}{a}\right)^2}. \quad \text{(Eq. 5)}$$

The foregoing equations can be used to model the magnetic field in regions close to array based on the pitch between the magnetized particles and their composition. Accordingly, a magnetic array can be designed to have a desired field strength and/or distance over which the magnetic field decays. Further discussion of the foregoing analytical framework can be found in "Calculation of the Field of a Lattice of Point Magnetic Dipoles" (E. V. Rozenfeld, Physics of the Solid State, 2000, 44, 1633-1640), which is incorporated herein by reference in its entirety.

FIG. 2b is a graph showing a one-dimensional (1D) slice of the magnetic force F (approximately $(B \cdot \nabla)B$) plotted versus x at a height d=a above the 2D lattice on which the simulation in FIG. 2a is based. In this plot, it can be seen that when d=a, the magnetic force is dominated by the first terms of the Fourier series, having a periodicity of a. At distances d>a/2, the (k, l)=(0, 1), (1, 0) components will dominate, creating traps with a periodicity of a. At distances d close to the lattice, higher frequency components become comparable in magnitude to the (0, 1) and (1, 0) harmonics, leading to magnetic traps with a size and periodicity less than a. In the limit of d→0, the Fourier series that describes the magnetic force approaches a 2D lattice of delta functions with a periodicity of a.

Figure 3:
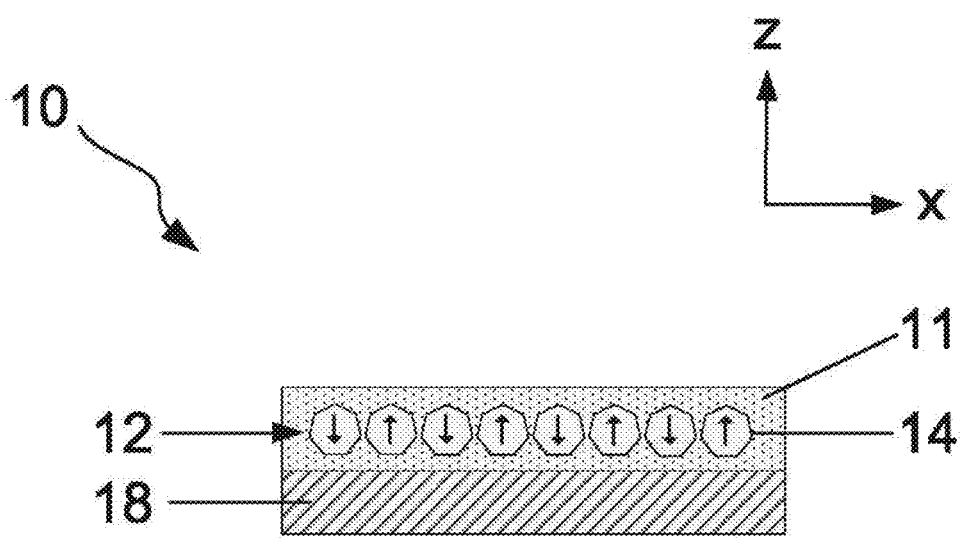
FIG. 3 is a schematic diagram that shows a cross-section of an exemplary self-assembled magnetic array device.

Various implementations of a device that employs an array of alternating magnetic dipole moments are possible. FIG. 3 shows a cross-section of an example device 10 that includes an array 12 of magnetized particles 14 suspended (i.e., fixed in place) in a suspension layer 11. The suspension layer 11 is positioned on a substrate 18. As with the array 2 shown in FIG. 1, the magnetized particles 14 are densely arranged in a lattice such that directly adjacent particles 14 are touching or nearly touching. The array 12 may extend in one, two, or three dimensions. A direction of a particle's magnetic dipole moment 16 (depicted by arrows in FIG. 3) alternates with respect to the direction of a directly adjacent particle's magnetic dipole moment 16. In this example, the suspension layer 11 surrounds each particle 14 in the array 12 such that the top and bottom surfaces of the particles 14 are covered with the layer 11. If a gap exists between directly adjacent particles 14, the layer 11 may also fill in those gaps. In some cases, the layer 11 also covers the surfaces of particles 14 located on the outer perimeter of the array 12.

In certain implementations, the thickness of the suspension layer 11 is slightly greater than the height of the particles 14 forming the array 12. For example, the thickness of the suspension layer 11 can range from anywhere between about 50 nm to about several millimeters, including, for example, about 100 nm, about 500 nm, about 1 μm, about 100 μm, or about 1 mm. The suspension layer 11 can be formed from materials including, but not limited to, polymers such as polydimethylsiloxane (PDMS), epoxy, polyurethane, SU-8 (available from MicroChem Corp.), poly (methyl methacrylate) (PMMA), and Norland optical adhesives (available from Norland Products Inc.). The substrate 18 can be formed from materials including, but not limited to, glass and plastics.

Methods of Manufacturing

In general, an array of magnetized particles can be fabricated as follows. Initially, magnetizable particles are combined with a liquid to produce a mixture. The mixture then is deposited on a supporting substrate. In some cases, the mixture may be spread out so that the particles form a layer having a thickness approximately equal to the size of one particle. The particles within the mixture are then magnetized. In some cases, the particles can be magnetized before the deposition on a supporting substrate. The magnetic fields of the newly magnetized particles cause the particles to move within the mixture so that the magnetic dipole moments are arrayed in an anti-parallel configuration. In some cases, the liquid then can be removed or, alternatively, solidified to form a suspension layer around the particles.

Figure 4:
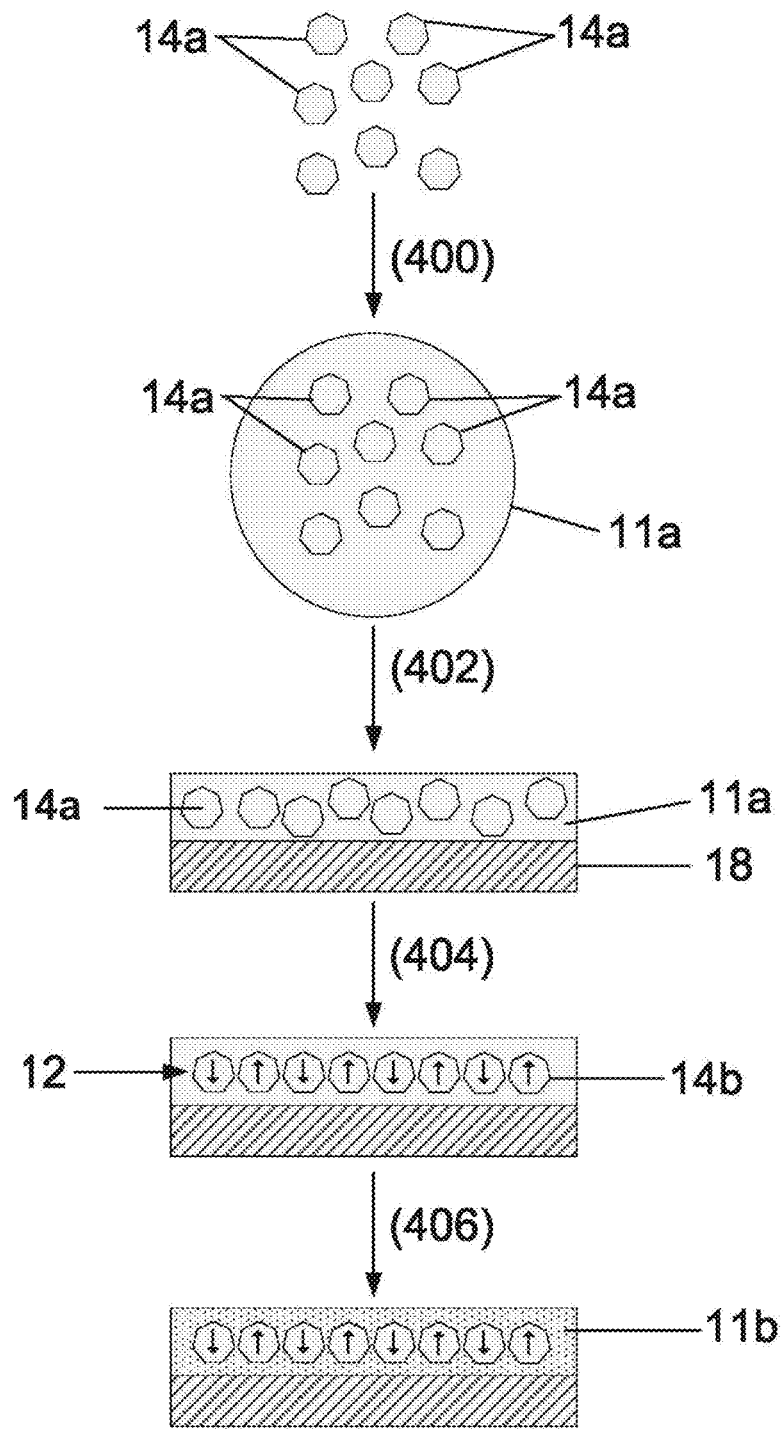
FIG. 4 is a schematic diagram that shows an exemplary process for fabricating the device illustrated in FIG. 3.

FIG. 4 shows an exemplary method of fabricating the device illustrated in FIG. 3. In the example, magnetizable particles 14a are first dissolved or suspended (400) in a suspension liquid 11a. The magnetizable particles 14 can be in the form of a powder such as the NdBFe powder (e.g., Magnequench, Toronto, Canada). The liquid 11a can be composed of, but not limited to, an uncured polymer, where the polymer can be cured by chemical activation or through the application of, e.g., light, heat or gas. Chemically curable polymers include polymers that can be hardened by mixing with a curing agent. Examples of chemically curable polymers include, but are not limited to, PDMS, polyurethane, epoxy, and PMMA. Cured PDMS is sometimes used to define the structural portions of microfluidic systems and devices. Thus, by incorporating the magnetizable particles 14a within PDMS used for a magnetic microfluidic device, as opposed to within a separate different layer, it is possible, in some implementations, to reduce the material costs as well as time associated with fabricating the microfluidic device. Ultraviolet (UV) curable polymers are a type of photo-curable polymers that can be patterned by applying UV light to the polymer, such as in photolithography. Certain UV curable polymers have very low viscosities which, as explained in more detail below, allow particles embedded in the suspension liquid 11a to be molded into tight geometries. In an exemplary implementation, the ratio, by weight, of PDMS to magnetizable particles, is about 10:1, which enables close-packing of the particles once magnetized. A greater proportion of PDMS to magnetizable particles would enable, in some implementations, sparser particle packing.

As explained previously in reference to FIG. 1, the magnetizable particles 14a can be formed from NdFeB, SmCo, ferrite, or superparamagnetic material. The amount of magnetizable particles 14a included in the suspension 11a can be selected such that, when the suspension liquid 11a is deposited on a substrate, the magnetizable particles 14a form a layer that is approximately equal to the thickness of one particle. Thus, in some cases, the amount of magnetizable particles 14a is a function of the area over which the suspension liquid 11a will be deposited. The proportion, by weight, of polymer to magnetizable material can range from about 5:1 to about 15:1 including, for example, about 6:1, 7:1, 8:1, 9:1, 10:1, 11:1, 12:1, 13:1, and 14:1. It should be noted, however, that the particles 14a are not yet magnetized (i.e., they do not exhibit a magnetic field) when placed in the suspension liquid 11a. This helps avoid the particles 14 from clumping together within the suspension liquid 11a due to magnetic attraction, which could otherwise occur if the particles 14a were magnetized.

The suspension liquid 11a, containing the magnetizable particles 14a, then is applied (402) onto a substrate 18. In some cases, the suspension liquid 11a is placed in a mold on substrate 18 in order to confine the area over which the polymer spreads. Alternatively, or in addition, suspension liquid 11 is physically spread out to ensure a uniform thickness. Once the suspension liquid 11a has been deposited on the surface of the substrate 18, and the particles have settled into a monolayer, the particles 14a are exposed to an external magnetic field (404) to become magnetized particles 14b. Alternatively, the particles 14a can be exposed to the external magnetic field prior to being deposited on the substrate. The magnitude of the applied magnetic field required to magnetize the particles 14a depends on the particle material and can include fields greater than 1 Tesla, including, for example, about 1.5 Tesla, about 2 Tesla, about 3 Tesla, about 4 Tesla, about 5 Tesla, about 6 Tesla, about 7 Tesla, about 8 Tesla, about 9 Tesla, or about 10 Tesla. Once magnetized, the particles 14b begin to minimize their overall magnetic energy by self-assembling into an array 12, in which a direction of each (or most of the) particle's magnetic dipole moment (indicated by arrows within particles 14b) alternates with respect to the direction of a directly adjacent particle's magnetic dipole moment. The magnetized particles 14b self-assemble by rotating and/or moving through the suspension liquid 11a.

The suspension liquid 11a is slowly cured (406) so that it becomes cross-linked to form a suspension layer 11b. In some cases, the curing process is performed at the same time the particles 14a are being exposed to the external magnetic field. Alternatively, the curing process can be performed subsequent to the magnetization of the particles 14a. By performing the curing process slowly, the magnetized particles 14b can have sufficient time to self-assemble into the ordered array 12. In some cases, the magnetized particles 14b self-assemble into a close-packed array. The cure time can depend on the type of polymer used, the curing process applied, as well as the thickness of the suspension layer 11b. As examples, the cure time can be about 30 minutes, 60 minutes, 120 minutes, or 180 minutes. Other cure times are possible as well. In addition, the increase in viscosity of the suspension liquid 11a during the curing process can, in some cases, help prevent the magnetized particles from clumping together during self-assembly. In other words, the increase in the polymer's resistance to flow may inhibit the magnetic attraction between magnetized particles 14b from pulling the particles together while still allowing the particles 14b enough movement to self-assemble into the ordered array 12.

Once cured, the magnetic and physical orientation of the particles is fixed so they can no longer move in the polymer. In some methods containing the fixed particles, the suspension layer 11b can be removed from the substrate 18 and moved into a device. Alternatively, the substrate can be part of a device.

Figure 5:
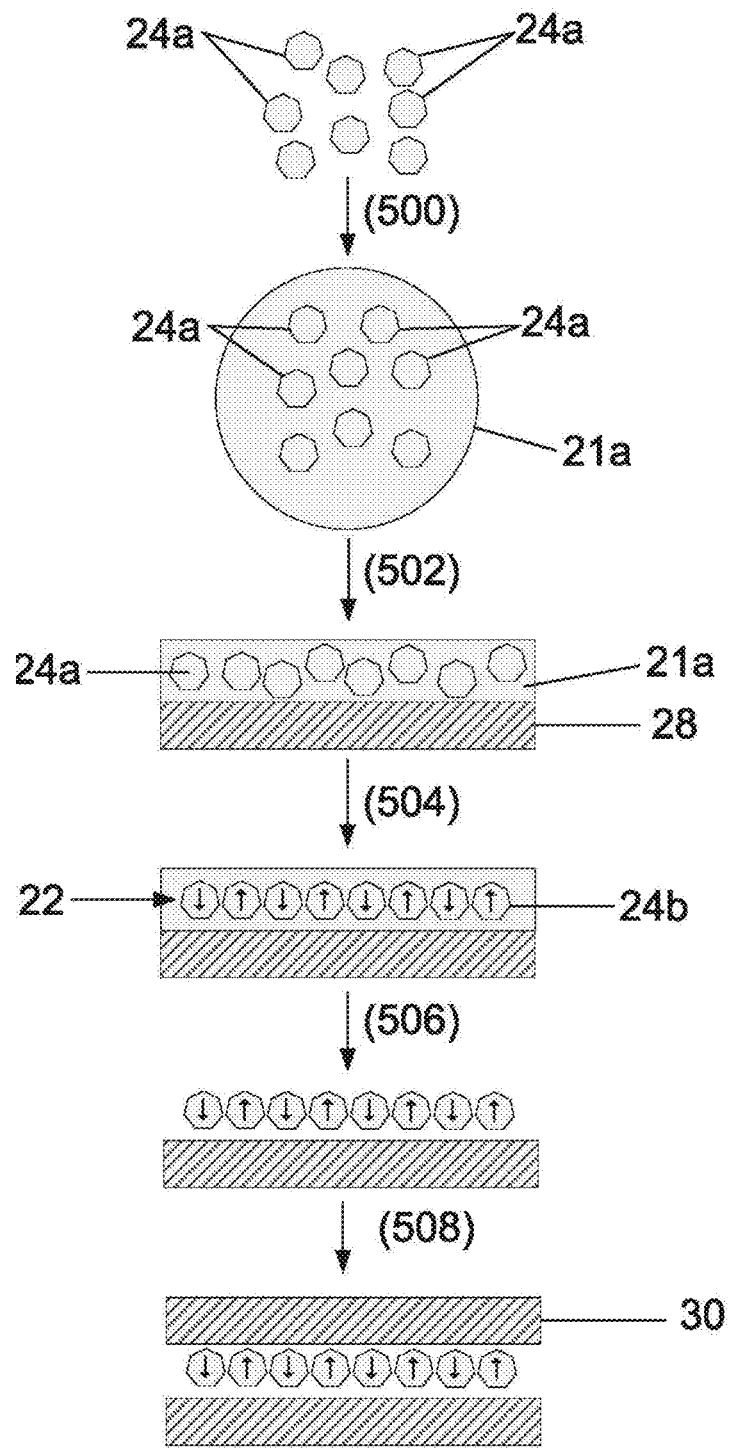
FIG. 5 is a schematic diagram that shows an exemplary process for fabricating a magnetic device having an array of self-assembled magnetic particles.

FIG. 5 shows an alternative method of fabricating a magnetic device having an array of self-assembled magnetic particles. Similar to the example illustrated in FIG. 4, the magnetizable particles 24a are first dispersed or suspended (500) in a suspension liquid 21a. However, instead of a polymer, the suspension liquid 21a is composed of a volatile solvent. For example, the solvent can include, but is not limited to, isopropanol, methanol, or ethanol. The amount of magnetizable particles 24a included in the suspension 21a can be selected such that, when the suspension liquid 21a is deposited on a substrate, the magnetizable particles 24a form a layer that is approximately equal to the thickness of one particle.

Subsequently, the mixture containing the suspension liquid 21a and the magnetizable particles 24a is deposited (502) on a surface of a substrate 28 including, for example, a plastic sheet such as Melinex® from DuPont. The suspension liquid 21a can be deposited by various means including, for example, pipetting or spin-coating the solution onto the substrate 28. Once the suspension liquid 21a has been deposited on the surface of the substrate 28, the particles 24a are exposed to an external magnetic field (504) to become magnetized particles 24b. Alternatively, in some cases, the particles 24a may be exposed to the external magnetic field prior to or simultaneously with depositing the suspension liquid 21a on the substrate 28. For example, the magnetic field can be applied to the substrate as the mixture is being deposited on the substrate's surface.

Once deposited the suspension liquid 21 spreads out on the substrate 28 due to surface tension effects or is physically spread out to ensure relatively uniform thickness. As explained in reference to the example of FIG. 4, the magnitude of the applied magnetic field required to magnetize the particles 24a depends on the particle material and can include fields greater than 1 Tesla including, for example, about 1.5 Tesla, about 2 Tesla, about 3 Tesla, about 4 Tesla, about 5 Tesla, about 6 Tesla, about 7 Tesla, about 8 Tesla, about 9 Tesla, or about 10 Tesla. Once magnetized, the particles 24b begin to minimize their overall magnetic energy by self-assembling into an array 22, where a direction of a particle's (e.g., each particle's) magnetic dipole moment (indicated by arrows within particles 24b) alternates with respect to the direction of each directly adjacent particle's magnetic dipole moment.

The solvent of the suspension liquid 21 is then evaporated (506), leaving the array 22 on the substrate 28. The evaporation process may be passive or may be enhanced by heating the substrate 28. Subsequently, a second layer 30 is placed (508) on top of the array 22 of magnetized particles 24b to seal the magnetic material. The second layer 30 may include another plastic sheet, such as Melinex®, which is coated with an adhesive (not shown) so it adheres to both the array 22 and the substrate 28. In some cases, the adhesive on the sheet 30 may fill gaps between directly adjacent magnetized particles 24b in the array.

Microfluidic Devices and Systems

In some implementations, the magnetic arrays depicted in the examples of FIGS. 1 and 3-5 can be incorporated into one or more microfluidic devices and/or systems. For example, the strong magnetic forces produced by the magnetic particles' exponentially decaying magnetic fields can, in some cases, be designed and/or combined with other components such as channels, pumps, valves, conduits, filters, controllers including hardware and/or software, sensors, imaging devices, among other components, to form systems that can be used to sort objects, such as cells, biomolecules, and other analytes that are inherently magnetic or that have been bound to a magnetic tag, e.g., ferrite and iron, flowing through a microfluidic channel based on the magnetic susceptibility of each of the objects or their tags in the channel. An advantage of using the magnetic arrays described in the present disclosure for separating chemicals, cells, and other objects is that the sorting can be performed in parallel, such that many cells are processed simultaneously.

Figure 6A:
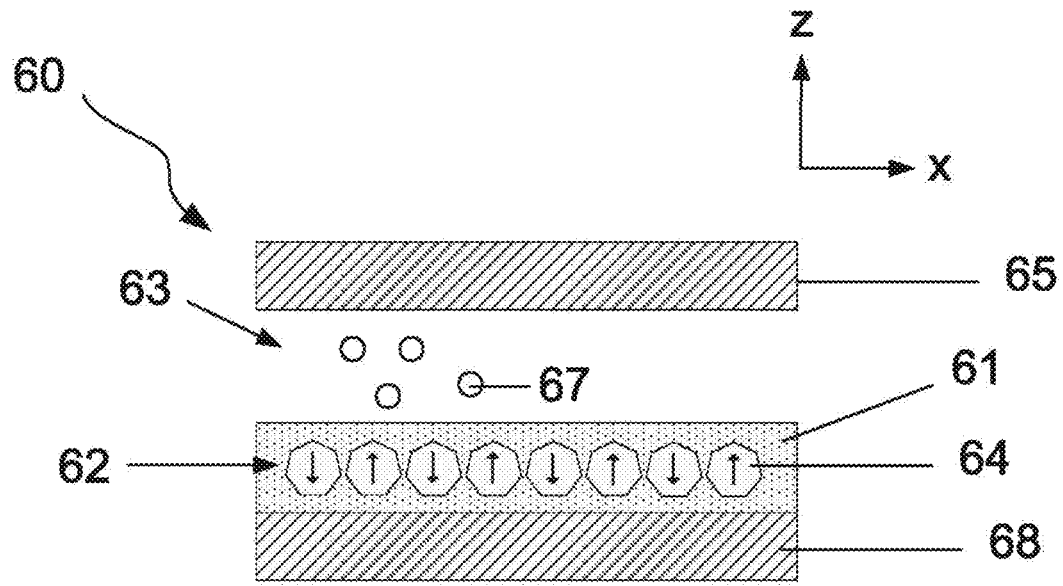
FIG. 6A is a schematic diagram that shows a cross-section of an exemplary microfluidic filtering device.

FIG. 6a shows a cross-section of an example of a microfluidic filtering device 60 that incorporates a self-assembled magnetic array 62 beneath the surface of a microfluidic channel 63. The array 62 of magnetic particles 64 can be formed from similar materials and using the same process described in reference to FIG. 4. As in the previous examples, the magnetic dipole moment direction of each particle in a majority of particles 64 in the array 62 alternates with respect to the magnetic dipole moment of a directly adjacent particle(s) 64 in the array 62. The magnetic particles 64 are fixed within a suspension layer 61 having a thickness approximately equal to the thickness of a single magnetic particle 64.

Figure 6B:
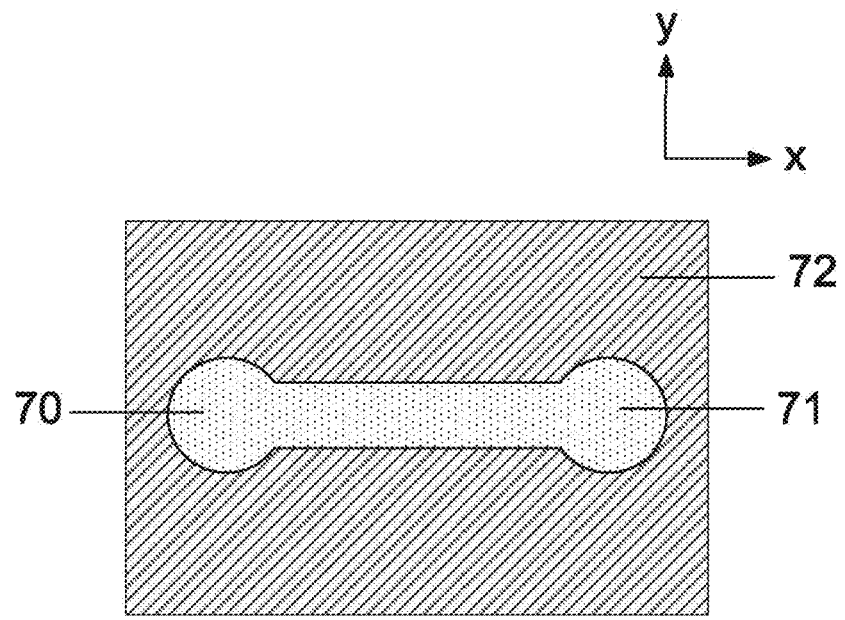
FIG. 6B is a schematic diagram that shows a top view of the exemplary microfluidic filtering device shown in FIG. 6A.

In the present example, the microfluidic device 60 also includes a sealing layer 65 to seal the microfluidic channel 63. In some cases, the microfluidic device can include a second array of self-assembled magnetic particles fixed within a suspension layer on top of the microfluidic channel 63 such that the second array serves to seal the channel 63 in place of the sealing layer 65. FIG. 6b shows a top view of the exemplary microfluidic filtering device 60 without the sealing layer 65. As shown in that example, the channel 63 can include an inlet port 70 for receiving fluid that passes through the channel and an outlet port 71 for discharging the same fluid. The channel 63 may be bound on either side by a layer of microfluidic compatible material 72, such as PDMS, glass, and epoxy photo-resists. In some implementations, the channel 63 is formed by depositing and curing a layer of polymer above the self-assembled magnetic array 62. The polymer is then etched to form the channel 63. Alternatively, the polymer can be deposited in a mold that defines the channel region and then transferred to the surface of the self-assembled magnetic array 62 once the polymer has been cured. In another example, the channel 63 can be formed by etching back the suspension layer 61 containing the magnetic particles 64 instead of adding an additional polymer layer. However, in such cases, the suspension layer 61 should be thick enough such that it is not etched through to the magnetic particles 64 in the array 62. In some implementations, the foregoing fabrication process and inexpensive device materials reduce manufacturing costs compared to devices that use non-disposable materials and/or materials which require lithography.

During use, a sample fluid containing one or more target analytes 67 is passed through the microfluidic channel 63. The target analytes 67 can include any object of interest that is small enough to pass through the channel 63, including, but not limited to, cells, molecules, proteins, and chemical compounds. The target analytes 67 can be selectively tagged (e.g., through covalent bonds, ionic bonds, or dipole-dipole interactions, among others) with magnetic markers, such as beads or nanoparticles, which are susceptible to the magnetic forces produced by the self-assembled magnetic array 62. As the target analytes 67 pass through the microfluidic channel 63 and adjacent to the array 62, the motion of the analytes 67 that are tagged with a magnetic marker will be altered by the magnetic forces produced by the array 62. In particular, the tagged analytes 67 will move towards the array 62 until they reach the bottom surface of the channel 63 closest to the array 62. The tagged analytes 67 will then remain essentially fixed to the surface of the channel 63 due to the magnetic forces of the array 62. Thus, the tagged analytes are separated or "filtered" from other analytes in the sample that are not themselves magnetic or have no magnetic marker.

The magnetic material that is used to tag analytes can include any superparamagnetic or permanent magnetic material. In some implementations, it is preferable to use magnetic material having a large magnetic moment given that such magnetic material can be trapped more easily by the magnetic forces produced by the array 62. Examples of magnetic material that can be used for tagging analytes includes, but is not limited to, manganese doped ferrite and iron. In some cases, the magnetic material used to tag target analytes in the microfluidic channel includes magnetic particles or beads. The maximum bead/particle size is limited by the microfluidic channel width and height, and by the size and nature of the analytes. Superparamagnetic nanoparticles can range in size from about 1 nm to about 200 nm. In some implementations, the object used to tag analytes is in the form of a multi-core bead/particle. In particular, the object includes an inner core formed from magnetic material and an outer shell formed from a separate different magnetic or non-magnetic material.

Modeling of the Magnetic Devices

Figure 7:
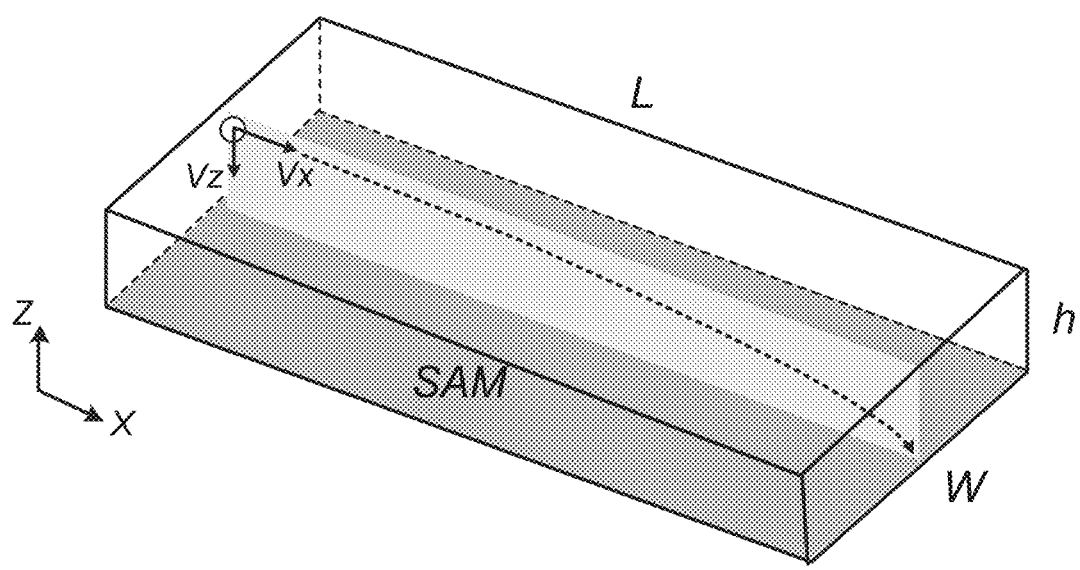
FIG. 7 is a schematic diagram that shows a simulation model of a microfluidic device having a self-assembled magnetic array as depicted in FIG. 6A.

FIG. 7 shows a simulation model used to characterize the flow of magnetic beads through a channel of a microfluidic device having a self-assembled magnetic (SAM) array as depicted in FIG. 6a. In this model, the magnetic force ($F_m$) of the magnetic array is balanced by the viscous drag of the fluid in the microfluidic channel. Thus, the velocity, $v_z$, of the magnetic object (radius r) can be written as $$F_m + 6\pi\eta r \cdot v_z = 0 \rightarrow v_z = -\frac{F_m}{6\pi\eta r}, \quad \text{(Eq. 6)}$$

where $\eta$ is the viscosity of the medium. The magnetic force decays exponentially in the z-direction. The far-reaching magnetic field is obtained from the boundary condition equation (see Eq. 5) with k=l=1 and using the relationship $F_m$ approximately equal to $(B \cdot \nabla)B$.

$$F_m \approx F_0 \exp\left[-\frac{4\sqrt{2}\pi}{a}z\right], \quad \text{(Eq. 7)}$$

where $F_0$ is the force right next to and on top of the self-assembled magnetic layer (i.e., z=0) and a is the pitch of the magnetic particles in the self-assembled magnetic layer. The z position of the magnetic object can be estimated using Eqs. 6 and 7, $$v_z = \frac{dz}{dt} = -\frac{F_0}{6\pi\eta r}\exp\left[-\frac{4\sqrt{2}\pi}{a}z\right] \rightarrow \int_H^0 \exp\left[\frac{4\sqrt{2}\pi}{a}z\right]dz = \quad \text{(Eq. 8)}$$

$$-\int_0^T \frac{F_0}{6\pi\eta r}dt \rightarrow \left(\frac{4\sqrt{2}\pi}{a}\right)^{-1}\left(e^{-\frac{4\sqrt{2}\pi}{a}H} - 1\right) = \frac{F_0}{6\pi\eta r}T,$$

The travel time of the magnetic bead is $T=L/v_x$ and the volume flow rate is $V_Q=w \cdot h \cdot v_x$. The maximum flow rate at which a device can still sustain the efficient capture of magnetic objects is then $$V_Q = \frac{F_0 w h L}{6\pi\eta r} \cdot \frac{4\sqrt{2}\pi}{a}\left(e^{\frac{4\sqrt{2}\pi}{a}H} - 1\right)^{-1}. \quad \text{(Eq. 9)}$$

An exemplary microfluidic device has a microfluidic channel width, w, of about 1 cm, a length, L, of about 1 cm, a height, h, of about 50 µm, and a pitch, a, between magnetic particles in the self-assembled array of about 125 µm. Based on the foregoing equations, the measured $F_0$ would be about 1 nN on magnetic beads (r=0.5 µm) flowing through water ($\eta$=0.8 mPa·s). Accordingly, such a device can support high speed flow of about 100 ml/hr.

Uses of the Magnetic Devices

The new devices and systems have many uses. One example of an application that can use the self-assembled magnetic arrays for sorting/filtering includes clearing bacteria in blood. In this example, the self-assembled magnet array can be combined with a microfluidic device to capture bacteria from whole blood to treat septic patients. The strong forces from the self-assembled magnetic array can be used to trap and remove magnetically tagged bacteria in the blood.

The self-assembled magnetic arrays as described herein are not limited to use in microfluidic sorting/filtering devices. Another application for which the self-assembled magnetic array can be used is magnetotransfection. Transfection is the process of deliberately introducing nucleic acid through a cell's membrane and into the cell. Genetic material (such as supercoiled plasmid DNA or siRNA constructs), or even proteins such as antibodies, can be transfected. Magnetotransfection is a transfection method that uses magnetic force to deliver DNA or proteins into target cells. In the case of DNA, nucleic acids are first tagged with magnetic nanoparticles. Then, application of a magnetic force drives the nucleic acid particle complexes towards and into the target cells, where the DNA is released. Using the self-assembled magnetic array of the present disclosure, a magnetotransfection device can be constructed in which the self-assembled magnetic array is located directly underneath a cell culture. The self-assembled magnetic array creates strong, localized magnetic field gradients that increase the transfection efficiency relative to that which can be achieved using external magnets.

Figure 8:
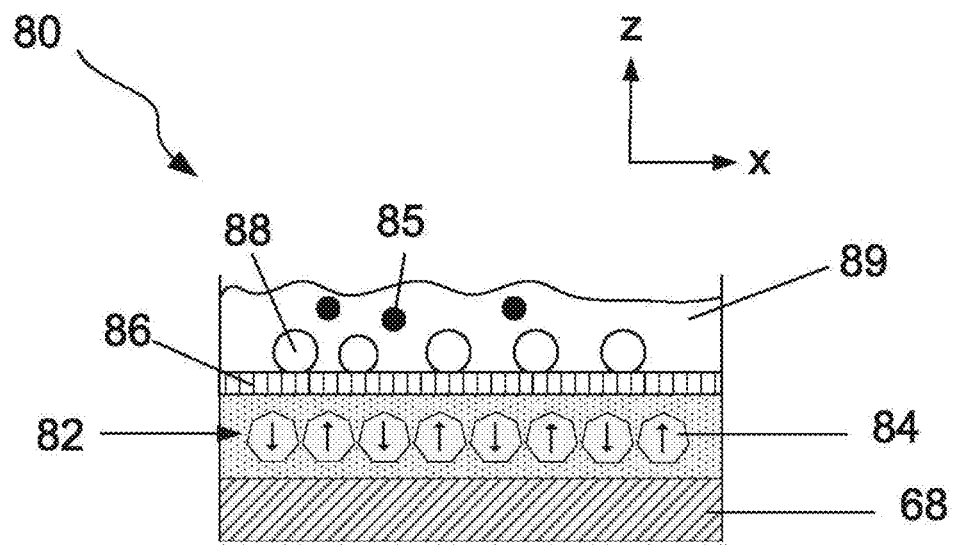
FIG. 8 is a schematic diagram that shows an example of a magnetotransfection device.

FIG. 8 shows an example of a magnetotransfection device 80 using a self-assembled magnetic array of the present disclosure. In this example, a cell culture medium 86 is positioned directly above an array 82 of self-assembled magnetic particles 84, where a magnetic dipole moment direction of each particle 84 in a majority of particles in the array 82 alternates with respect to the magnetic dipole moment direction of a directly adjacent particle(s) 82 in the array. The cell culture medium 86 includes cells 88 bound to the surface of the culture medium and within distance of the strong magnetic fields produced by the array 82. In addition, the cell culture medium 86 is submerged within a cell culture solution 89. Genetic material (not shown) bound to magnetic nanoparticles 85 in the cell culture solution 89 is pulled downward toward the cells 88 by the strong magnetic forces generated by the array 82 and subsequently forced through the cells' membranes. Examples of cell culture media include, but are not limited to, Basal Media, RPMI Medium, Minimum Essential Medium, and Dulbeco's Modified Eagle Medium.

Another exemplary application is to use the self-assembled magnetic array to purify small molecules from one or more biological specimens. In particular, magnetic nanoparticles can be coated with affinity ligands to selectively bind to proteins or nucleic acids. The tagged proteins or nucleic acids then can be removed from the biological specimen using the strong magnetic field gradients of the self-assembled magnetic array such that a high purity and enriched sample is obtained. The captured molecules then can be released by cleaving the affinity ligands on the nanoparticles.

In some implementations, the self-assembled magnetic arrays can be used to generate polarizing fields in magnetic sensors. For example, the self-assembled magnetic arrays can be used to generate strong magnetic fields for nuclear magnetic resonance (NMR) spectroscopy. In NMR spectroscopy, target analytes, such as isotopes, proteins, or chemical compounds, are placed in a magnetic field and subsequently exhibit absorption of the field at frequencies that are characteristic to the target. Analysis of the resulting NMR spectrum provides information on the number and type of chemical entities in the target. In another example, the self-assembled magnetic array can be used in a magnetoresistance sensor. A magnetoresistance sensor detects the change in value of a material's electrical resistance in response to the application of an external magnetic field. The self-assembled magnetic array can be used as the magnetic source for generating the external magnetic field of such sensors.

EXAMPLES

The invention is further described in the following example, which does not limit the scope of the invention described in the claims.

Example 1

Figure 9:
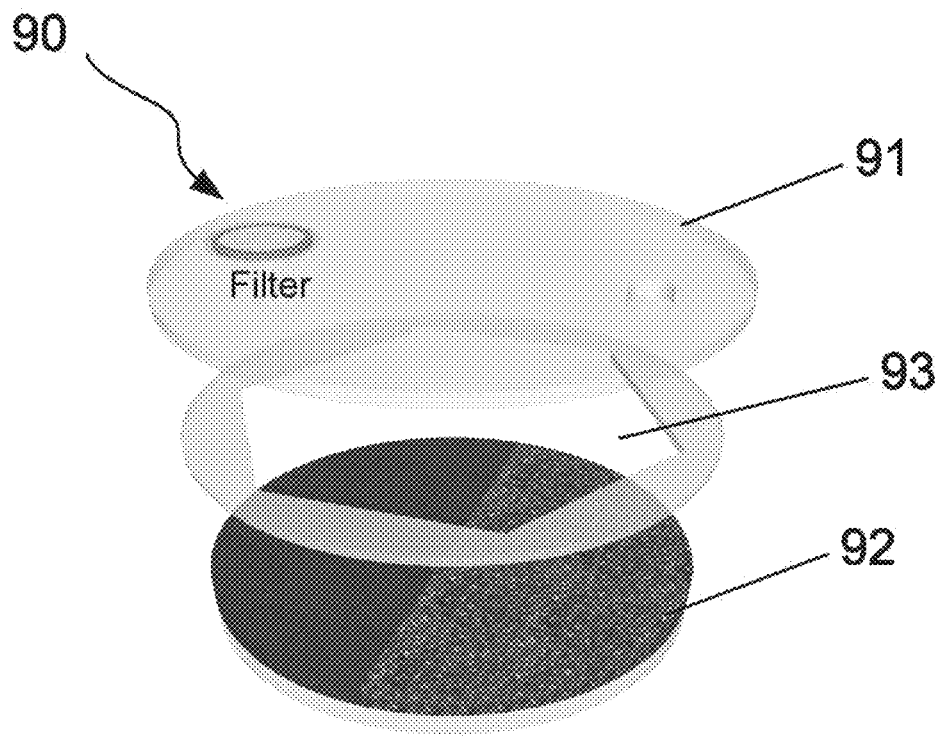
FIG. 9 is a schematic diagram that shows an exploded view of a prototype filter utilizing a self-assembled magnetic array.

To demonstrate the technique of using self-assembled magnets, a prototype self-assembled magnetic array filter 90 was fabricated. FIG. 9 shows an exploded view of the prototype filter 90. The filter includes a PLEXIGLAS® lid 91 and a magnetic assembly containing a self-assembled layer 92 of permanent magnets integrated below a microfluidic channel 93. To implement the self-assembled magnetic layer, NdFeB powder (obtained from Magnequench) was suspended in uncured PDMS (polydimethylsiloxane) and magnetized using a high-field magnet (e.g., exhibiting a magnetic field greater than about 1 T). Subsequently, the mixture was slowly cured (about 1 hour) to allow for the self-assembly of NdFeB grains. A microfluidic channel was then built directly on top of the cured magnet using a 50 μm thick layer of two-sided adhesive coated polyester film (MELINEX® obtained from DuPont). The channel patterns were defined via laser-cutting using a laser (VLS3 laser obtained from VersaLaser) for fast prototyping. A lid/sealing layer was constructed using a 1.5 mm thick extruded PMMA sheet (e.g., PLEXIGLAS® obtained from McMaster Carr). Holes for the input port and output port were defined with the laser cutter. Additionally, a membrane filter with 5 μm pores (e.g., NUCLEPORE® obtained from Whatman) was sealed over the output hole using a layer of laser-cut polyester film. The membrane filter captured cells for optical inspection after the magnetic separation step.

Figure 10:
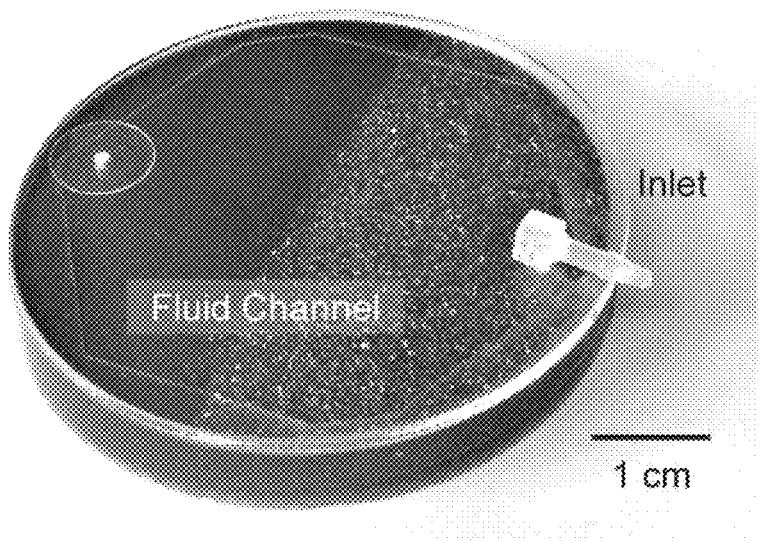
FIG. 10 is a photograph of a prototype filter utilizing a self-assembled magnetic array.

FIG. 10 shows a photograph of the prototype self-assembled magnetic array filter system. The device has two magnetic sections for efficient cell capture. At the entry port, the self-assembled magnetic array layer is made of 125 μm grains of NdFeB. The 125 μm grain layer creates a magnetic field that extends throughout the channel height, pulling the cells towards the bottom of the channel. Further along the channel, the magnetic particle grain size was reduced to 8 μm to create a stronger, but shorter range force to firmly trap cells.

To evaluate the capability of the self-assembled magnetic array filter for cell sorting, negative enrichment of tumor cells suspended in an abundant population of leukocytes was performed. The samples were prepared by mixing a known amount of leukocytes and tumor cells. Leukocytes were harvested from a mouse spleen by dissociating the tissue followed by red blood cell lysis. Tumor cells (SK-BR-3, breast carcinoma) were cultured in McCoy's medium, supplemented with 10% fetal bovine serum (FBS), penicillin and streptomycin (1%), L-glutamine (1%), and maintained at 37° C. in a humidified atmosphere containing 5% of $CO_2$.

For quantitative analysis of cell separation by the self-assembled magnetic array filter, flow cytometry on the samples was performed before and after sorting. Leukocytes were stained green with carboxyfluorescein succinimidyl ester (CFSE obtained from Invitrogen). Briefly, the cells, having a concentration of approximately $10^7$/ml, were incubated at room temperature with 1 μM CFSE for 10 min. The incubation was stopped with 100% FBS and the cells were triple-washed before spiking with tumor cells. SK-BR-3 cells, having a concentration of approximately $10^6$/ml, were stained with 1 μM CellTracker™ Red CMPTX (obtained from Invitrogen). The two cell populations were mixed at different ratios and incubated with protein tyrosine phosphatase, receptor type, C antigen (CD45) magnetic beads (MACS® beads obtained from Miltenyi Biotec) at 4° C. for specific labeling of leukocytes. The cell mixtures were subsequently fixed in formaldehyde and passed through the self-assembled magnetic array filter.

The utility of the self-assembled magnetic array filter as a practical tool to concentrate and detect rare cells from a large background population was demonstrated using a microfluidic device with an integrated membrane filter. In this operation, the population of leukocytes and tumor cells were concurrently labeled in a single incubation step. Samples were prepared by mixing leukocytes (pre-stained with CFSE) and SK-BR-3 cells at different ratios. The cell mixtures were then incubated simultaneously with CD45 magnetic beads to specifically target leukocytes and fluorescently-labeled HER2/neu antibodies (Hercpetin obtained from Genentech) to tag SK-BR-3 cells. The samples were then processed with the self-assembled magnetic array filter to deplete leukocytes and hence enrich tumor cells. SK-BR-3 cells, collected and retained on the membrane filter, were imaged using a fluorescence microscope (Eclipse 80i obtained from Nikon).

Figure 11B:
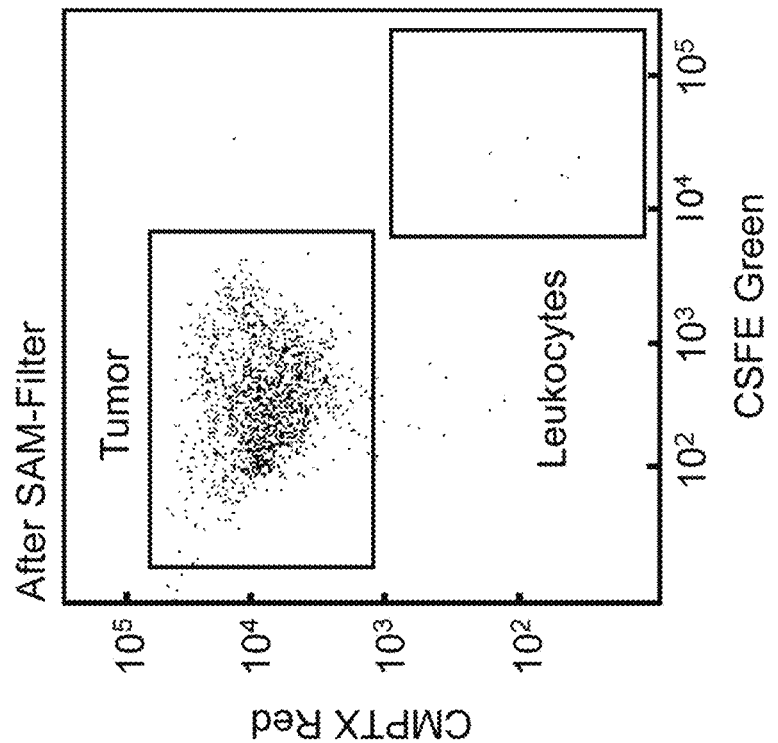
FIGS. 11A and 11B are graphs that show a change in the composition of a suspension before and after filtering through a self-assembled magnetic array, respectively.
Figure 11A:
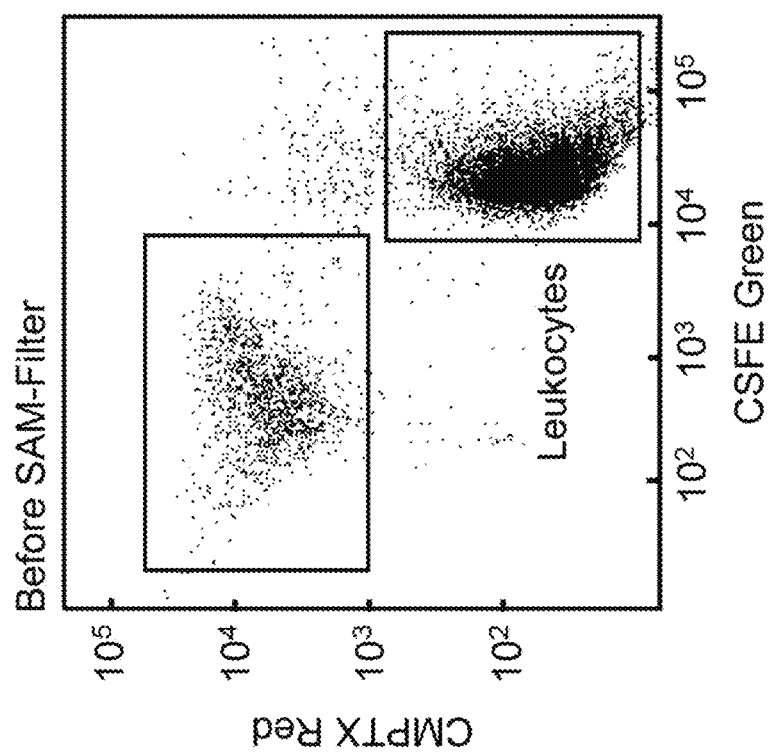

FIGS. 11a and 11b show the change in the composition of the suspension before and after filtration, respectively, as measured by flow cytometry. The leukocytes were stained with a CSFE green dye and the tagged with magnetic beads.

Figure 12:
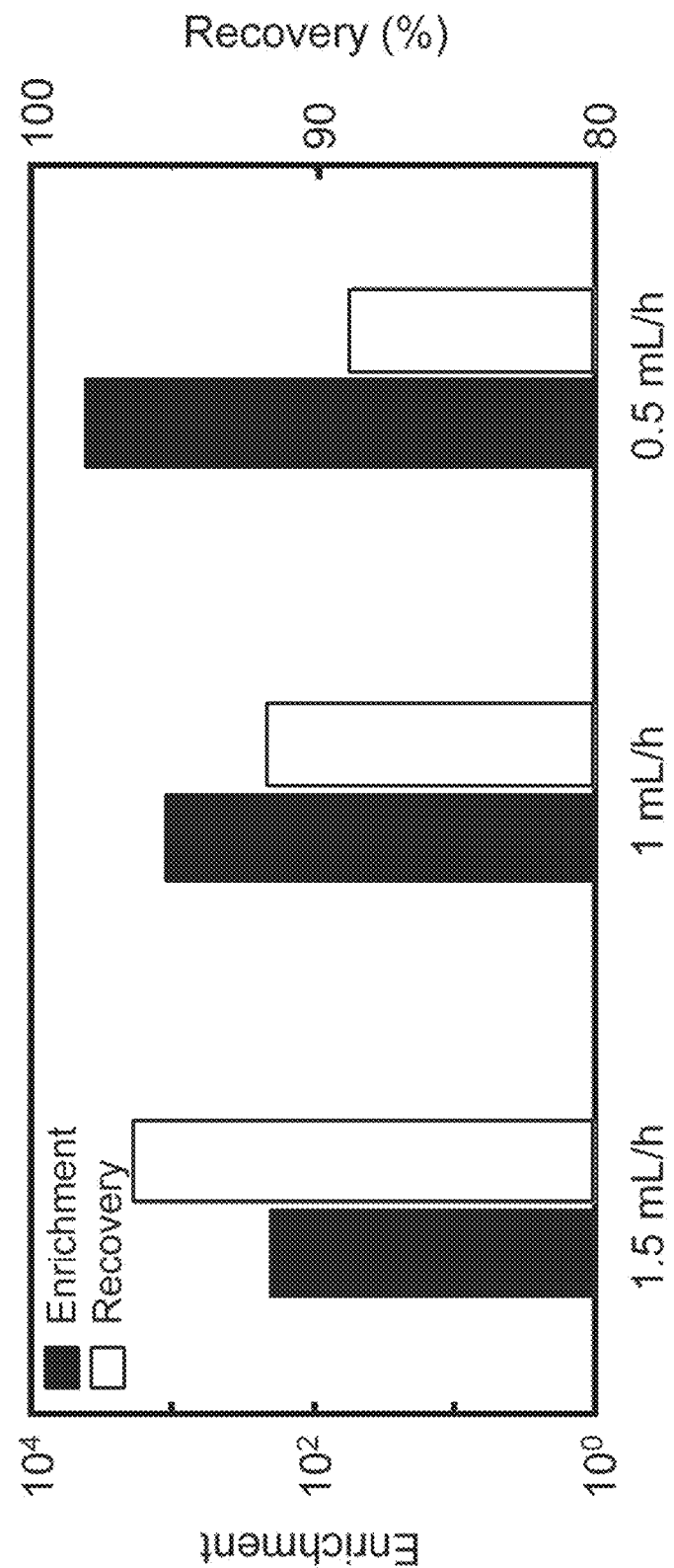
FIG. 12 is a bar graph that depicts a level of enrichment and recovery ratio of a self-assembled magnetic array filter for several different flow rates of a suspension through a self-assembled magnetic array filter.

The tumor cells were stained with a CMPTX red dye. The horizontal axis of each graph corresponds to the concentration of the leukocytes stained with the CSFE green dye whereas the vertical axis in each graph corresponds to the concentration of the tumor cells stained with the CMPTX red dye. The two graphs show that, subsequent to filtration with the magnetic array filter, the concentration of leukocytes decreases substantially. FIG. 12 is a bar graph that depicts enrichment and recovery ratio of the self-assembled magnetic array filter for several different flow rates of the suspension. The self-assembled magnetic array filter again showed high capturing efficiency, enriching the population of tumor cells to leukocytes by a factor of about $10^3$. The recovery ratio of the self-assembled magnetic array filter, the fraction of tumor cells that pass through the system, was approximately 90%. In this example, the enrichment and recovery ratio are shown to depend on the flow rate of the solution through the device, with the recovery ratio decreasing with decreasing flow rates and the enrichment ratio increasing with decreasing flow rates.

The utility of the self-assembled magnetic array filter to detect rare cells was demonstrated by repeating the experiment mentioned above, but this time using the single-step incubation and an integrated membrane filter to concentrate the tumor cells for optical inspection. A suspension of tumor cells and leukocytes were incubated concurrently with CD45 antibody conjugated magnetic beads that bind to the leukocytes, and fluorescently labeled antibody that selectively tag tumor cells. FIG. 13 illustrates an example of the conjugation and tagging process. The suspension was passed through the self-assembled magnetic array filter to deplete leukocytes and to concentrate tumor cells on the membrane filter at the output port. FIGS. 14a-14f are fluorescence micrographs of the input and the output of a self-assembled magnetic array filter for suspensions with initial concentration ratios of 1/10, 1/100, and 1/1000 (tumor/leukocytes). The self-assembled magnetic array filter effectively depleted the leukocytes from the suspension, enabling sparse tumor cells to be separated and concentrated for facile detection.

Example 2

Figures 15A, 15B:
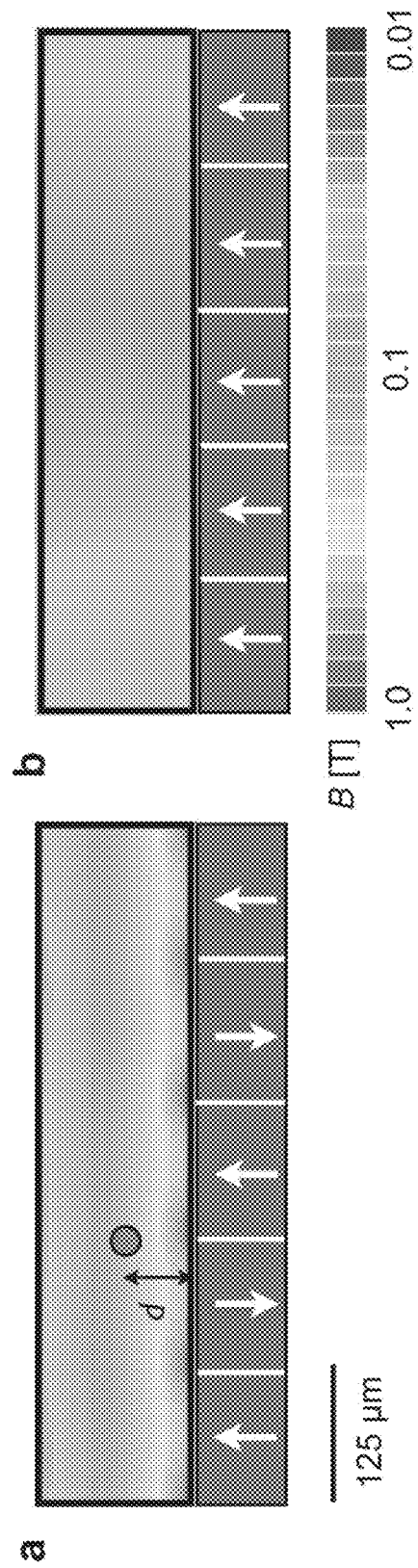
FIG. 15A is a graph that shows a simulation of magnetic field strength B plotted against the cross-section of a microfluidic device.
FIG. 15B is a graph that shows a simulation of magnetic field strength B plotted against the cross-section of a microfluidic device.

Magnetic field simulations were used to aid the design and characterization of the prototype self-assembled magnetic array filter. FIG. 15a shows a simulation of magnetic field strength B plotted on the cross-section of the microfluidic channel of an ideal system of anti-aligned magnetic dipoles within a self-assembled magnetic array. The magnetic field strength drops rapidly in distance from the surface of the magnetic layer, creating large gradients that lead to strong magnetic forces. In contrast, FIG. 15b shows a simulation of the magnetic field strength plotted on the cross-section of the microfluidic channel of an ideal system of aligned magnetic dipoles. The strong gradients of the self-assembled magnet can be seen in contrast to the weak gradients created when the magnetic grains are all aligned in the same direction. The simulation geometry was modeled on a self-assembled magnetic array filter having 125 µm sized NdFeB dipoles embedded in PDMS, below a 50 µm thick channel of water. The NdFeB material was modeled as being fully magnetized with the saturation magnetization $M_p$=875 kA/m. Finite element simulations (using Maxwell® simulation software from Ansoft) were used to find the magnetic vector field B, from which the magnetic forces were calculated.

Figure 16:
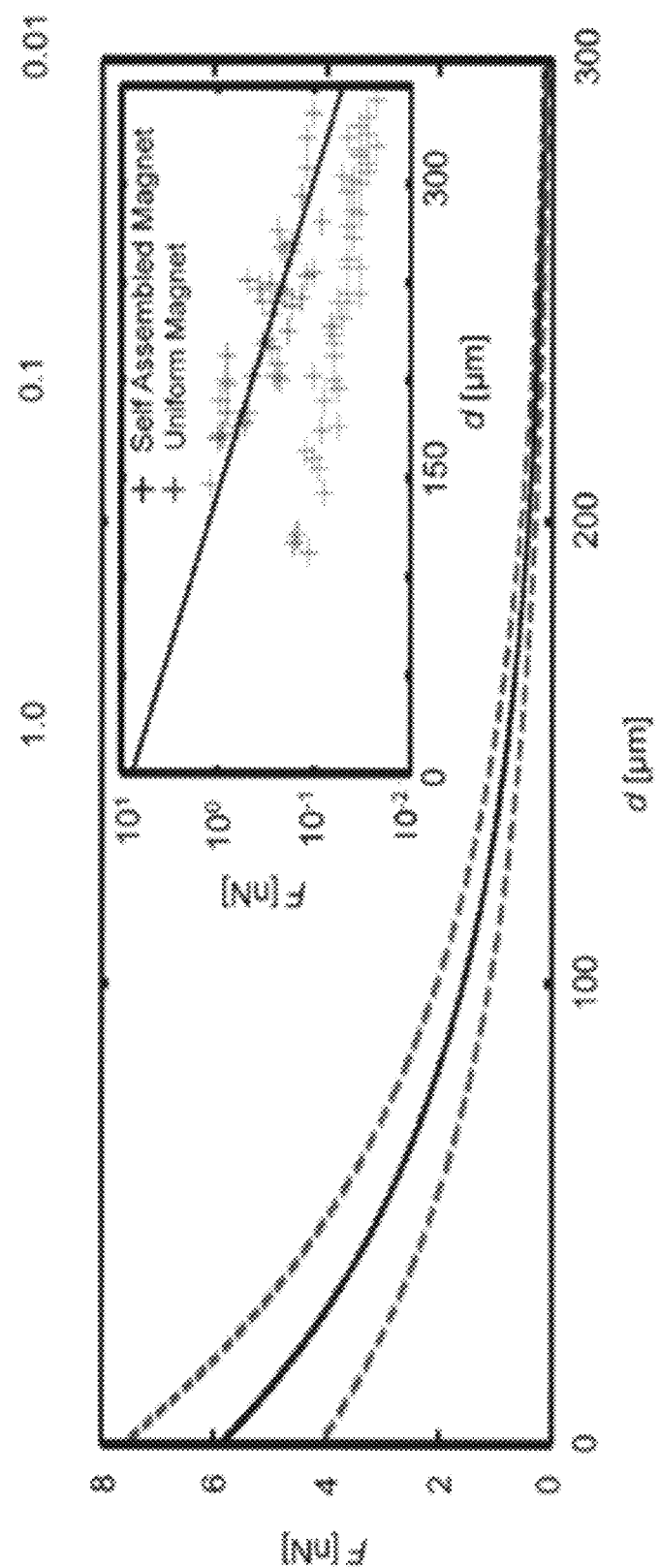
FIG. 16 is a graph that shows force versus distance from a magnet's surface.

The magnetic force from the prototype self-assembled magnetic array filter was measured by optically tracking the motion of magnetic beads (Dynabead® 653-05 obtained from Invitrogen) in the fluidic channel. The force (F) was calculated by measuring the velocity v of the beads as a function of distance d from the magnet, using Stoke's law (F=6πηrv), where η=0.8 mPa·s is the viscosity of the solution and r=0.5 µm is the radius of the bead. FIG. 16 shows a graph depicting an exponential decay function fitted to the measured force versus distance from the magnet's surface. As shown in the plot, the force decays exponentially with distance from the magnet's surface, thus agreeing with the model of alternating magnetic dipoles. The inset of FIG. 16 shows the experimentally measured force on magnetic beads as a function of their distance from a self assembled magnet (black) and a uniformly magnetized magnet (red). The dotted red lines in FIG. 16 indicate the upper and lower bounds of the fit to the measured. Furthermore, the magnitude of the force is approximately 10 nN, which is consistent with the results of the numerical simulation, and is about 100 times larger than found in known lithographically-patterned magnets. When compared to a control magnet in which all magnetic grains are magnetized in the same direction, the self-assembled magnet exerted forces about 50 times larger, verifying that force enhancement with the self-assembled magnetic array filter was due to the anti-parallel arrangement of magnetic dipoles.

Example 3

The efficiency of the self-assembled magnetic array filter was tested by sorting magnetic beads from non-magnetic polystyrene beads. A suspension that contained 2 µm diameter fluorescent polystyrene beads (FluroSpheres® F8826 obtained from Invitrogen) and 1 µm diameter fluorescent magnetic beads (Dynabead® 653-05 obtained from Invitrogen) were passed through the prototype self-assembled magnetic array filter. As a negative control, identical suspensions were processed using a self-assembled magnetic array filter with non-magnetized NdFeB. The change in the composition of the suspension before and after the filtration was quantified by flow cytometry (using LSR II flow cytometer obtained from BD Biosciences). Immediately before flow cytometry, samples were spiked with a concentration of polystyrene beads (FluroSpheres F8825 obtained from Invitrogen) of a third color. The purpose of this "counter bead" was to provide a controlled reference; the composition of non-magnetic and magnetic beads was measured with $10^5$ counts of the counter beads. The performance of the self-assembled magnetic array filter was gauged using two parameters: enrichment ratio:

$$(C_p^1/C_m^1)/(C_p^0/C_m^0)$$

and recovery ratio:

$$C_p^1/C_p^0,$$

where $C_p^0$ and $C_p^1$ are the concentration of polystyrene beads before and after sorting respectively, and $C_m^0$ and $C_m^1$ are the concentration of magnetic beads before and after sorting respectively.

Figure 17B:
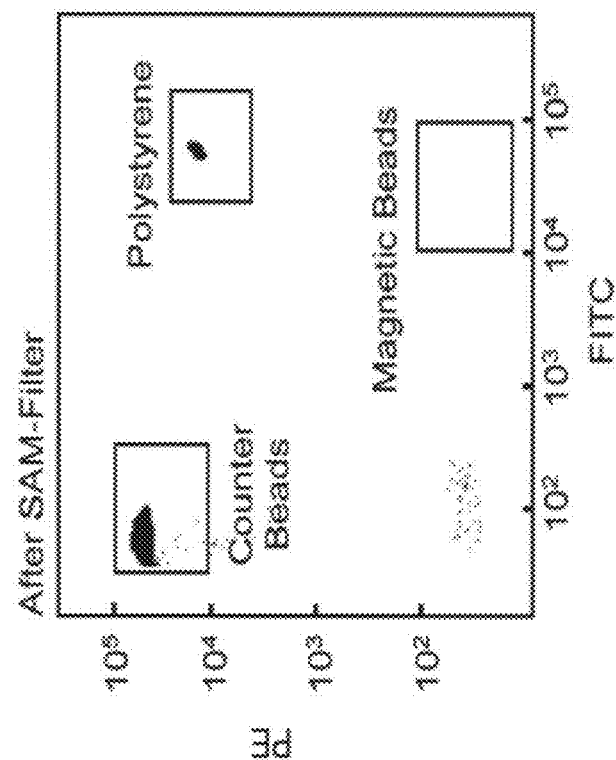
FIGS. 17A and 17B are graphs that show the detection of phycoerythrin (PE) and fluorescein isothiocyanate (FITC) fluorescence before and after filtering through a self-assembled magnetic array filter, respectively.
Figure 17A:
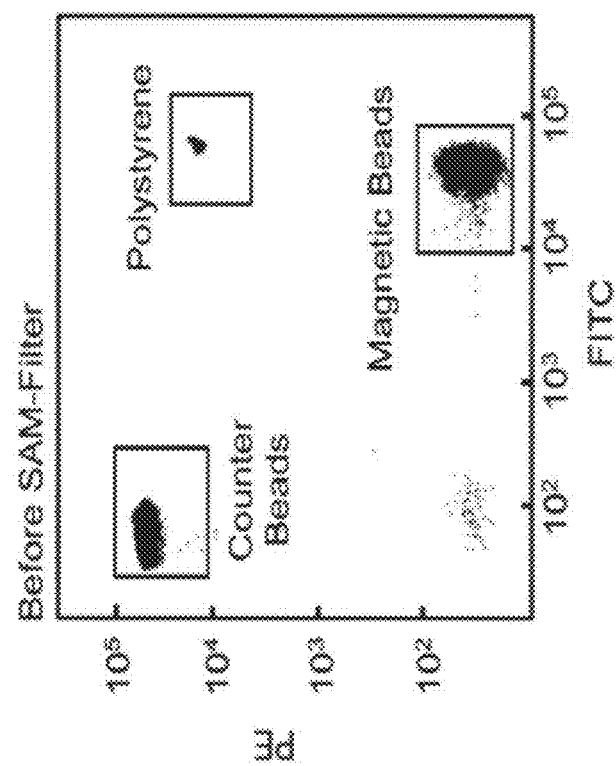
Figure 18:
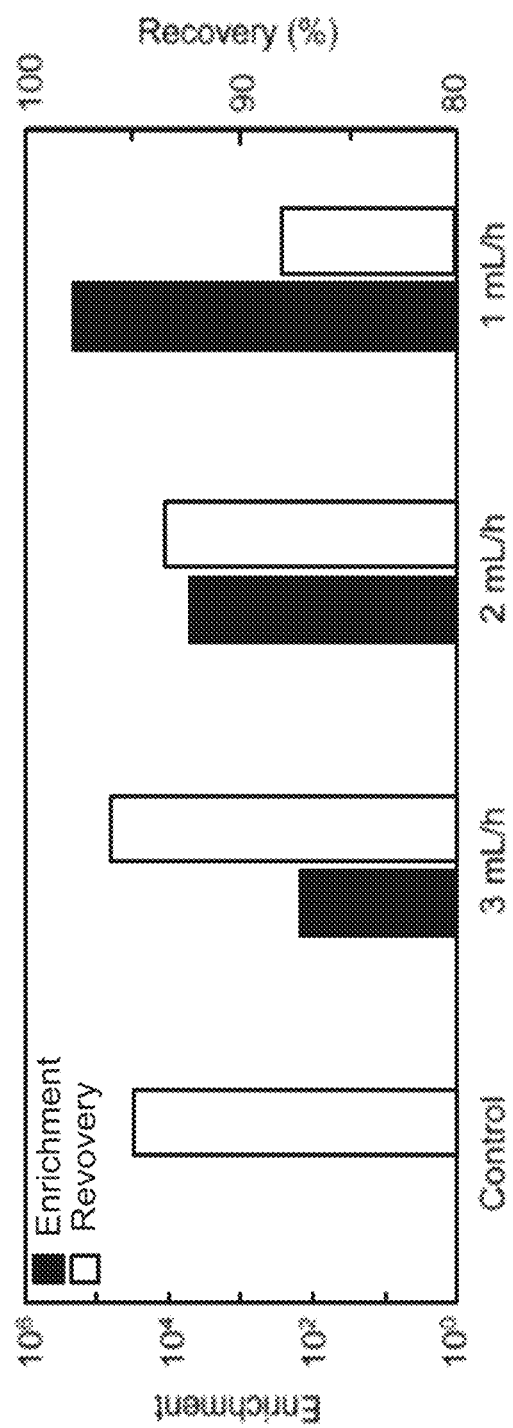
FIG. 18 is a bar graph that depicts a level of enrichment and recovery ratio for several different flow rates through a self-assembled magnetic array filter.

FIGS. 17a and 17b show the results of flow cytometry before filtration and after filtration. In particular, FIG. 17a shows the counts of fluorescent detection of phycoerythrine (PE) from non-magnetic beads and fluorescein isothiocyanate (FITC) from magnetic beads before filtering. FIG. 17b shows the changes of fluorescent counts after filtering. As can be seen from the two graphs, essentially all of the magnetic beads have been filtered. FIG. 18 is a bar graph that depicts enrichment and recovery ratio for several different flow rates through the self-assembled magnetic array filter. As shown in these results, the magnetic filter can exhibit a very high capturing efficiency, enriching the population of nonmagnetic beads by a factor of about $10^5$. The recovery ratio, i.e., the fraction of non-magnetic beads that make it through the system, was approximately 90%. In contrast, the negative control, using the non-magnetized NdFeB, showed negligible enrichment (equal to about 1). Due to the strong magnetic force, the self-assembled magnetic array filter could achieve high capture efficiency even at moderately high flow rates of 1 mL/hr. In addition, as shown in this example, the recovery ratio tends to decrease with a decrease in the flow rate of solution through the device.

In other words, as the flow of fluid through the channel slows, non-magnetic objects will occupy more time inside the channel leading to an increase in the probability that they will stick to the device surface (for example, through non-specific binding). In contrast, the enrichment ratio tends to increase with a decrease in the flow rate of solution as magnetic particles spend more time in the channel and thus increase the probability that they will be influenced by the magnetic force from the self-assembled magnetic array.

Other Embodiments

It is to be understood that while the invention has been described in conjunction with the detailed description thereof, the foregoing description is intended to illustrate and not limit the scope of the invention, which is defined by the scope of the appended claims. For example, in some implementations, the magnetized particles in an array can be arranged/magnetized such that most or all of the particles have a magnetic dipole moment that is in the same direction as a magnetic dipole moment of a directly adjacent particle or particles in the array. Although such configurations have weaker magnetic fields than the configurations where the dipole moments alternate, the resulting magnetic field will extend further and decay more slowly away from the array. This type of field can be advantageous, for example, when the height of an adjacent microfluidic channel is large. In this arrangement, the particles are fixed in place, and then magnetized, thus ensuring that all of the dipole moments are pointing in the same direction.

Figures 19A, 19B:
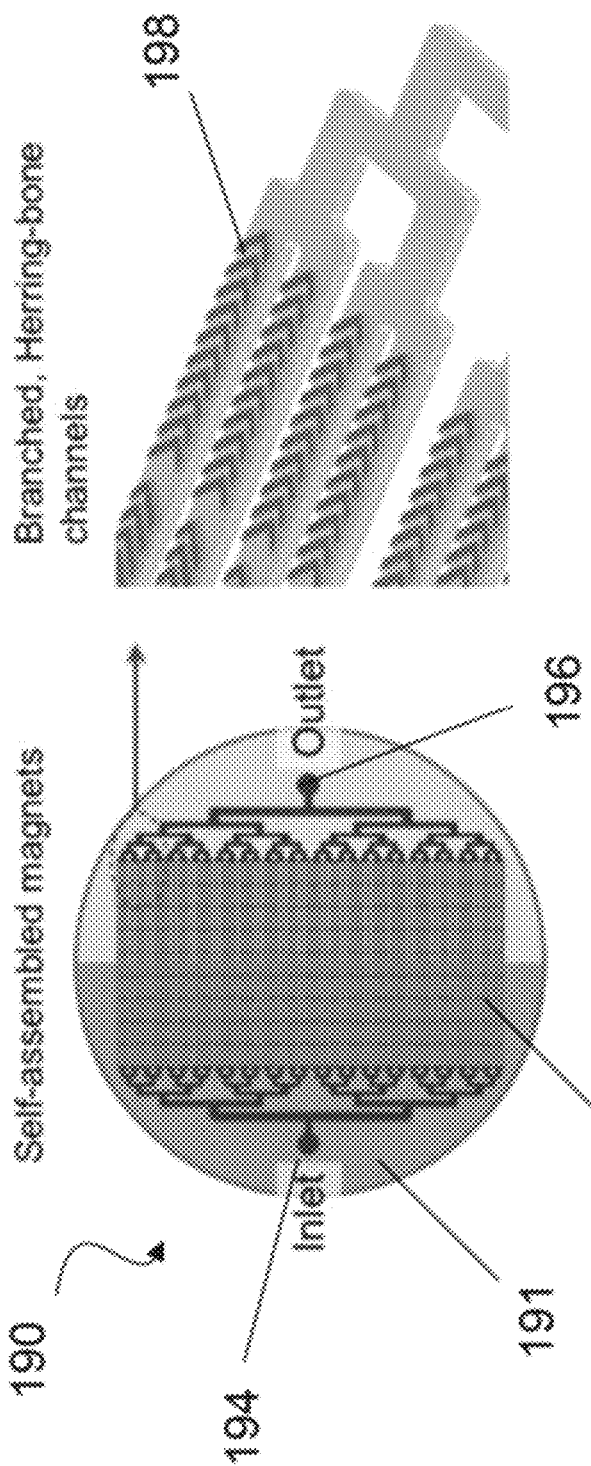
FIG. 19A is a schematic top view of an example of a microfluidic filtering device.
FIG. 19B is a schematic illustrating examples of chaotic mixers in channels of the microfluidic filtering device of FIG. 19A.

In some implementations, the prototype self-assembled magnetic array filter can include multiple channels as opposed to a single channel. FIG. 19A is a schematic top view of an example of a microfluidic filtering device 190 that includes a self-assembled magnetic array beneath the surface of multiple parallel arranged microfluidic channels 192. The shaded region 191 on the left side of the device indicates the location of the array of the magnetic particles beneath the channels. The magnetic particle array can be formed from similar materials and using the same process described in reference to FIG. 4. As in the previous examples, the magnetic dipole moment direction of each particle in a majority of particles in the magnetic array alternates with respect to the magnetic dipole moment of a directly adjacent particle(s) in the array. The fluid enters the channels 192 from an inlet port 194 and exits the device through an outlet port 196.

In the present example, the microfluidic device 190 includes 64 substantially parallel fluidic channels, each of which is approximately 400 μm wide and 150 μm in height. The channels are enclosed using solid PDMS and separated from one another by approximately 50 μm wide barriers. By substantially parallel channels, it is meant that the channels are parallel to each other within a degree of tolerance enabled by the channel manufacturing process. The use of the multiple narrow parallel channels helps ensure that the fluid flow in the direction of the outlet is substantially uniform across the width of each channel and across the width of the device.

In addition, one or more, e.g., each channel 192 in the example device 190 can include one or more chaotic mixers 198. FIG. 19B is a schematic illustrating examples of the chaotic mixers that can be included in the channels of the device 190. The chaotic mixers 198 include branched, herring-bone shaped features formed along one or more sides of the channels. In some implementations, the chaotic mixers create a downward force that drives particles in the fluid closer to the magnetic array, such that the particles can interact with the magnetic field generated by the array. As a result, the addition of chaotic mixers 198 to the fluid channels allows the height of the channel to be increased, thus leading to an increase in the amount of fluid passing through each channel.

Figure 20A:
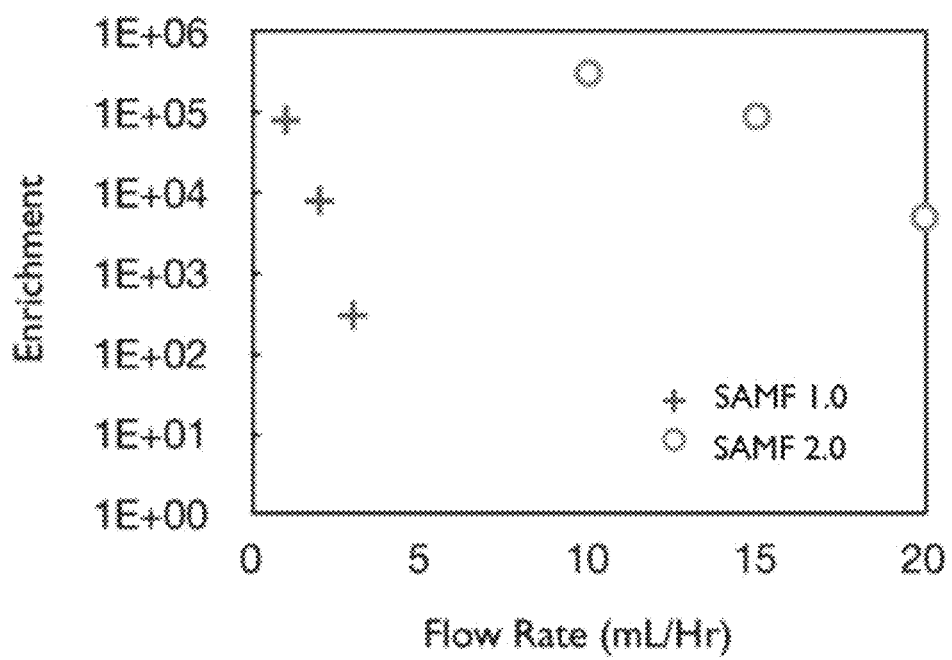
FIG. 20A is a plot of particle enrichment versus flow rate.
Figure 20B:
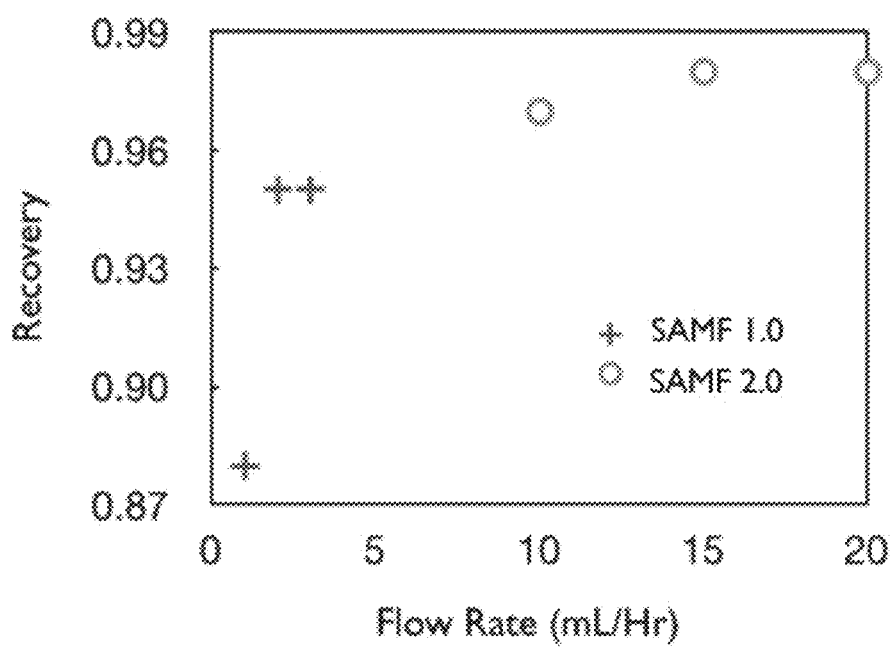
FIG. 20B is a plot of particle recovery versus flow rate.

Accordingly, using the multiple channels and chaotic mixers, device 190 can provide an improved enrichment and cell recovery ratio compared to the device 90 shown in FIGS. 9-10. For example, FIG. 20a is a plot of particle enrichment versus flow rate comparing the performance of the self-assembled magnet flow (SAMF) device 90 (SAMF 1.0) and the SAMF multi-channel device 190 (SAMF 2.0). A PDMS fluid containing magnetic beads and polystyrene beads was passed from an input to an output of each device. As shown in the plot, magnetic particle enrichment in device 90 (corresponding to cross-markers) begins to decline as the flow rate approaches 5 ml/hr. In contrast, device 190 enables substantially higher cell enrichment values (corresponding to circle-markers) even at flow rates of 20 ml/hr. Similarly, FIG. 20b is a plot of particle recovery versus flow rate comparing the performance of SAMF device 90 (SAMF 1.0) with SAMF multi-channel device 190 (SAMF 2.0). As shown in the plot, maximum particle recovery for device 190 (corresponding to cross-markers) is several percent higher than the maximum particle recovery for device 90 (corresponding to circle-markers). Other aspects, advantages, and modifications are within the scope of the following claims.

What is claimed is:

1. A magnetic device comprising:
    a substrate;
    an array including a plurality of magnetic particles arranged in a single layer on the substrate, wherein a magnetic dipole moment direction of each magnetic particle in a majority of the magnetic particles alternates with respect to a magnetic dipole direction of a directly adjacent magnetic particle in the array, wherein an average maximum dimension of each particle of the plurality of magnetic particles is between about 50 nm to about 125 microns, and wherein directly adjacent particles within the array are separated by a spacing of 5 nm or less;
    a fluid flow channel having a bottom surface arranged adjacent to the array, wherein the magnetic dipole moment direction of each magnetic particle in the majority of the magnetic particles is oriented substantially orthogonal to the bottom surface of the fluid flow channel.

2. The magnetic device according to claim 1, wherein the magnetic particles in the array comprise permanent magnets.

3. The magnetic device according to claim 1, wherein the magnetic particles in the array comprise a superparamagnetic material.

4. The magnetic device according to claim 1, wherein the magnetic particles in the array comprise one or more of NdFeB, SmCo, FePt, and iron oxide.

5. The magnetic device according to claim 1, further comprising a suspension layer, wherein the array of magnetic particles is located in the suspension layer.

6. The magnetic device according to claim 5, wherein the suspension layer comprises a curable polymer.

7. The magnetic device according to claim 6, wherein the polymer comprises polyurethane, epoxy, poly(methyl methacrylate) (PMMA), or polydimethylsiloxane (PDMS).

8. The magnetic device according to claim 1, further comprising:
   a sheet coated with an adhesive that adheres to the array of magnetic particles.

9. The magnetic device according to claim 1, wherein the plurality of magnetic particles in the array is close-packed.

10. The magnetic device according to claim 1, further comprising a plurality of fluid flow channels arranged adjacent to the array.

* * * * *